(12) United States Patent
Horwitz et al.

(10) Patent No.: US 7,060,818 B2
(45) Date of Patent: Jun. 13, 2006

(54) SYNTHESIS OF MACROCYCLIC TETRAAMIDO COMPOUNDS AND NEW METAL INSERTION PROCESS

(75) Inventors: Colin P. Horwitz, Pittsburgh, PA (US); Anindya Ghosh, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 10/371,591

(22) Filed: Feb. 21, 2003

(65) Prior Publication Data

US 2004/0167329 A1    Aug. 26, 2004

(51) Int. Cl.
C07D 225/00 (2006.01)
C07D 295/00 (2006.01)
C07D 245/00 (2006.01)
C07D 487/00 (2006.01)
C07D 255/02 (2006.01)

(52) U.S. Cl. ............ 540/450; 540/473; 540/474; 540/545

(58) Field of Classification Search ........... 540/450, 540/473, 474, 545
See application file for complete search history.

(56) References Cited

U.S. PATENT DOCUMENTS

| | | | |
|---|---|---|---|
| 4,517,122 A | 5/1985 | Tomalia et al. | |
| 4,577,042 A | 3/1986 | Collins et al. | |
| 4,758,682 A | 7/1988 | Collins et al. | |
| 4,923,985 A * | 5/1990 | Gansow et al. | 540/474 |
| 5,189,160 A | 2/1993 | Memeger, Jr. | |
| 5,247,075 A | 9/1993 | Parker et al. | |
| 5,298,618 A | 3/1994 | Speranza et al. | |
| 5,445,755 A | 8/1995 | Convents et al. | |
| 5,474,576 A | 12/1995 | Thoen et al. | |
| 5,785,886 A | 7/1998 | Kerschner et al. | |
| 5,847,120 A | 12/1998 | Collins et al. | |
| 5,853,428 A | 12/1998 | Collins et al. | |
| 5,876,625 A | 3/1999 | Collins et al. | |
| 6,051,704 A | 4/2000 | Gordon-Wylie et al. | |
| 6,054,580 A | 4/2000 | Collins et al. | |
| 6,099,586 A | 8/2000 | Collins et al. | |
| 6,127,536 A | 10/2000 | Deline et al. | |
| 6,136,223 A | 10/2000 | Collins et al. | |
| 6,241,779 B1 | 6/2001 | Collins et al. | |
| 6,297,400 B1 | 10/2001 | Deline et al. | |
| 6,384,279 B1 | 5/2002 | Deline et al. | |
| 2002/0134965 A1 | 9/2002 | Danjo | |
| 2003/0168630 A1 | 9/2003 | Carlina et al. | |

FOREIGN PATENT DOCUMENTS

| | | |
|---|---|---|
| WO | WO 94/12621 | 6/1994 |
| WO | WO 94/21777 | 9/1994 |
| WO | WO 95/31526 | 11/1995 |
| WO | WO 97/29174 | 8/1997 |
| WO | WO 97/48787 | 12/1997 |
| WO | WO 98/39405 | 9/1998 |
| WO | WO 02/16330 A1 | 2/2002 |
| WO | WO 03/014277 A1 | 2/2003 |
| WO | WO 03/014279 A1 | 2/2003 |
| WO | WO 03/014280 A1 | 2/2003 |

OTHER PUBLICATIONS

McGraw-Hill-Dictionary of Chemical Terms, © 1984 by McGraw-Hill, Inc., p. 251.*
Grant & Hackh's Chemical Dictionary, 5th ed. © 1987 by McGraw-Hill, Inc. p. 347.*
Hawley's Condensed Chemical Dictionary, © 1997 by Van Nostrand Reinhold, pp. 587 and 687.*
Okuno et al, "A Convenient Method for the Synthesis of Macrocyclic Tetra-amides by Double Condensation Reaction" J. Chem Soc. Perkin Trans. I, vol. 5, pp. 1115-1118 (1984).*
The Merck Index, 13th ed., Merck & Co., Inc. Whitehouse Station, NJ USA © 2001. p. 1791.*
Dale et al, "The Chemical Development of the Commercial Route to Sildenafil: A Case History" Organic Process Research and Development, vol. 4, pp. 17-200 (2000).*
Al-Hassan, S. S. et al., Specific Inhibitors in Vitamin Biosynthesis. Part 7. Synthesis of Blocked 7,8-Dihydropteridines via α-Amino Ketones, J. Chem. Soc., Perkin Trans. 1 1985, pp. 1645-1659.
Bradshaw, J. S. et al., Aza-Crown Macrocycles, Chap IV, p. 146, John Wiley & Sons Inc., 1993.

(Continued)

*Primary Examiner*—James O. Wilson
*Assistant Examiner*—Zachary C. Tucker
(74) *Attorney, Agent, or Firm*—Kirkpatrick & Lockhart Nicholson Graham LLP

(57) ABSTRACT

An improved method of synthesizing a macrocyclic tetraamido compound includes protecting the amino portion of an amino carboxylic acid to form a protected amino carboxylic acid; exposing the protected amino carboxylic acid to a first solvent, preferably a hydrocarbon solvent, such as toluene or 1,2-dichloroethane, dichloromethane, dibromomethane and 1,2-dibromoethane. The carboxylic acid portion of the protected amino carboxylic acid is then converted to an activated carboxylic acid by one of esterification or acid halide formation, to form a protected amino activated carboxylic acid derivative. The protected amino activated carboxylic acid derivative is reacted with a diamine in the presence of a second solvent, such as THF or ,2-dichloroethane, dichloromethane, dibromomethane and 1,2-dibromoethane, to form a protected diamide diamine intermediate. Following deprotection, the diamide diamine intermediate is reacted with an activated diacid, such as an activated malonate, oxalate or succinate derivative to form the macrocyclic tetraamido compound. The macrocyclic tetraamido compound may further be complexed with a transition metal.

46 Claims, No Drawings

OTHER PUBLICATIONS

Buschmann, J. et al., The Structures of Difluorodiisocyanatomethane, $CF_2(NCO)_2$: X-ray Crystallography, Gas Electron Diffraction, and Quantum Chemical Calculations, Phys. Chem. A 2000, 104, pp. 7123-7128.

Bushby, R. J. et al., The Introduction of Alkylidene Substituents into the 4-Position of the 3,3,5,5-Tetramethyl-Δ-pyrazoline Nucleus by the Thioketone plus Diazoalkane Reaction: Synthesis of Tetrasubstituted Episulphides and Alkenes, J. Chem. Soc., Perkin Trans. 1, pp. 2401-2408, 1979.

Collins, T. J., Designing Ligands for Oxidizing Complexes, Department of Chemistry, Carnegie Mellon University, Accounts of Chemical Research, 1994, 27, pp. 279-285.

Drake, N. L. et al. Synthetic Antimarlarials, Some Derivatives of 8-Aminoquinoline, Laboratories of the University of Maryland, vol. 68, Aug. 1946, pp. 1536-1543.

Fletcher, G. A. et al., A List of Amino-Acid Derivatives Which Are Useful in Peptide Synthesis, Int. J. Peptide Protein Res. 4, 1972, pp. 347-371.

Greene, T. W., Protective Groups in Organic Synthesis, Chap. V, pp. 154-192, Chap. VII, pp. 218-287, Harvard University, John Wiley & Sons, 1981.

Kozmin, A. S. et al., Opening of the Three-Membered Ring of Derivatives of Cyclopropane-1, 1-Dicarboxylic Acid in the Reaction with Hydazine Hydrate, trans. from Zhumal Organicheskoi Khimii, vol. 7, No. 10, p. 2224, Oct., 1971, Journal of Organic Chemistry of U.S.S.R., pp. 2309-2310.

Keinan, E. et al., Diiodosilane. 3. Direct Synthesis of Acyl Iodides from Carboxylic Acids, Esters, Lactones, Acyl Chlorides, and Anhydrides, J. Org. Chem. 1990, 55, pp. 3922-3926.

Krapcho, A. P. et al., α—Carbalkoxylations of Carboxylic Acids, A General Synthetic Route to Monoesters of Malonic Acids, Tetrahedron Letters No. 32, pp. 2721-2723, 1974.

Larock, R. C., Comprehensive Organic Transformations: A Guide to Functional Group Preparations, Wiley-VCH, New York, 2nd ed., 1999, pp. 1941-1954.

Nakamura, M. et al., Fluorimetric Determination of Aromatic Aldehydes With 4,5-Dimethoxyl-1,2-Diaminobenzene, Analytica Chimica Acta, 134, 1982, pp. 39-45.

* cited by examiner

SYNTHESIS OF MACROCYCLIC TETRAAMIDO COMPOUNDS AND NEW METAL INSERTION PROCESS

CROSS-REFERENCE TO RELATED APPLICATION

Not Applicable.

STATEMENT REGARDING FEDERALLY SPONSORED RESEARCH

Not Applicable.

BACKGROUND OF THE INVENTION

The present invention is directed to an improved method for synthesizing macrocyclic tetraamido compounds and insertion of a transition metal ion into the ligand structure.

DESCRIPTION OF THE INVENTION BACKGROUND

Complexes of high oxidation state transition metals are known to function as oxidants in numerous biological reactions under the influence of a protein matrix. A widespread interest in understanding the mechanism of action and the reactivity of certain monooxygenase catalysts has led to the development of a series of metal-containing catalytic oxidant activators that have been shown to be useful in a variety of diverse industries.

Collins, T. J., "Designing Ligands for Oxidizing Complexes," *Accounts of Chemical Research,* 279, Vol. 27, No. 9 (1994), describes a design oriented approach for obtaining ligands that are resistant to oxidative degradation when coordinated to highly oxidizing metal centers. Several diamido-N-diphenoxido and diamido-N-alkoxido acyclic chelate compounds and macrocyclic tetraamido-N chelate compounds are described in the Collins *Accounts of Chemical Research* article. Significant improvements in the macrocyclic tetraamido design and applications for its use in diverse industries are described in Collins, et al., U.S. Pat. Nos. 5,847,120, 5,876,625, 5,853,428, 6,054,580, and 6,136,223.

An azide based synthetic route to macrocyclic tetraamido compounds is described in Uffelman, E. S., Ph.D. Thesis, California Institute of Technology, (1992).

The yield of the azide based method is about 25% for the final ring closing step but only about 5–10% for the combined sequence of steps. This method generates new C—N bonds via formation of azide intermediates. The generation of the C—N bonds, however, is not very effective, at least as to yield. With each step of the process, the yield is reduced further so that the overall yield of the desired tetraamido ligand is comparatively low. Furthermore, the azide based method produces high energy intermediates.

An alternative method of producing tetraamido macrocyclic compounds was described in Gordon-Wylie et al., U.S. Pat. No. 6,051,704. This method involves generally two main steps: reacting an amino carboxylic acid with an activated oxalate or malonate derivative in the presence of a supporting solvent and heat, and adding thereto a diamine, or a protected diamine, in the presence of a solvent and a coupling agent, again with heat, to form the tetraamido macrocyclic compound. In a further step, a transition metal is coupled to the amides of the macrocyclic compound in the presence of a solvent.

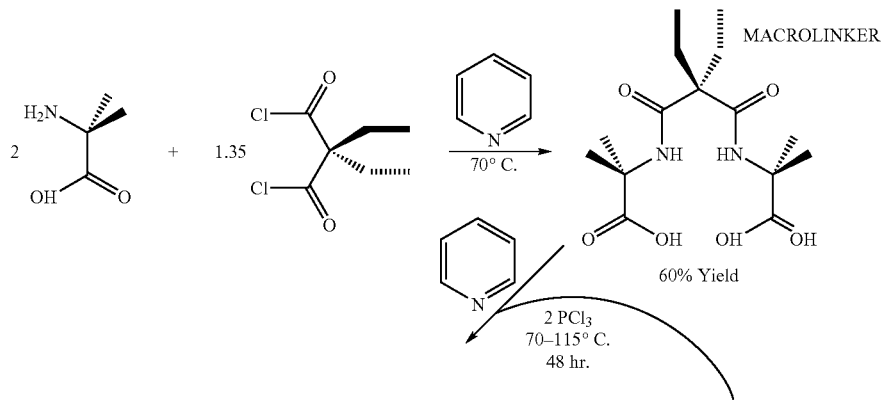

-continued

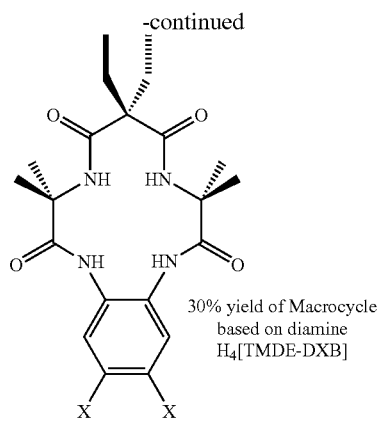

30% yield of Macrocycle based on diamine H4[TMDE-DXB]

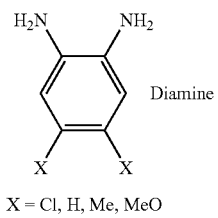

Diamine

X = Cl, H, Me, MeO

The method described in the '704 patent has proved difficult to convert to large-scale production for industrial use of the macrocyclic tetraamido compounds. The yields are too low and the solvents used are not favored for industrial scale production.

An alternative method for synthesizing macrocyclic tetraamido ligands is the subject of U.S. Pat. Nos. 6,127,536, 6,297,400, and 6,384,279.

There is a need for a more efficient and cost effective method for synthesizing macrocyclic tetraamido compounds.

SUMMARY OF THE INVENTION

An improved method for making a macrocyclic tetraamido compound is provided. The method comprises protecting an amino portion of an amino carboxylic acid at a first temperature sufficient to form the protected amino carboxylic acid; combining the protected amino carboxylic acid with a first solvent; converting the carboxylic acid portion of the protected amino carboxylic acid to an activated carboxylic acid derivative, preferably by esterification or acid halide formation, to form a protected amino activated carboxylic acid derivative; reacting the protected amino activated carboxylic acid derivative with a diamine in the presence of a second solvent to form a protected diamide diamine intermediate; deprotecting the diamide diamine intermediate; and, reacting the diamide diamine intermediate with an activated diacid to form the macrocyclic tetraamido compound. An activated carboxylic acid derivative, as used herein, shall refer to a carboxylic acid derivative that reacts with a primary amine to form a secondary amide.

In one embodiment of the method, protecting the amino portion of the amino carboxylic acid may be done by reacting the amino carboxylic acid with an anhydride, such as those selected from the group consisting of phthalic anhydride, substituted phthalic anhydride, and 2,3-diphenylmaleic anhydride.

In an embodiment of the method, wherein toluene is chosen as the first solvent, the protected amino carboxylic acid is poured into the toluene. In another embodiment of the method of the invention, the first solvent is a dihaloalkane. In this embodiment, the dihaloalkane is added to the protected amino carboxylic acid. Examples of suitable dihaloalkanes include 1,2-dichloroethane, dichloromethane, 1,2-dibromoethane and 1,2 dichloromethane. In either case, the second solvent may be THF or a dihaloalkane. The second solvent is used in the presence of a base, such as triethylamine or other tertiary amine or heterocyclic bases like pyridine.

The acid halide formation may comprise reacting the protected amino carboxylic acid with an organic acid chloride or bromide, or inorganic acid chloride or bromide, or $H_2SiI_2$. A particularly suitable acid chloride is thionyl chloride, which, when used, is preferably present in amounts ranging from about 0.9 to 1.5 molar equivalents relative to the amino carboxylic acid. In one embodiment of the method of the invention, the thionyl chloride and the protected amino carboxylic acid are heated to reflux for periods of time ranging from about 1 to about five hours, depending on the nature of the first solvent used. Those skilled in the art will recognize that other means of acid halide formation will provide an activated carboxylic acid derivative.

Activating the carboxylic acid portion of the amino carboxylic acid by esterification may comprise reaction with an ester forming reagent, such as $BF_3.Et_2O$ and the like.

The diamine may be selected from the group consisting of n,n+1 alkyl diamines, 1,2-aryl diamines, substituted n,n+2 alkyl diamines, substituted o-amino benzylamines and substituted 1,8-diamino napthalenes.

The diamine of the method may be selected from the group consisting of substituted and unsubstituted phenylene diamines. The substituted phenylene diamine may be 1,2-amino-4,5-X phenylene, wherein X is selected from the group consisting of H, amino, halo, nitro, alkyl, alkoxy and amido, and 1,2-amino-4-X phenylene, wherein X is selected from the group consisting of H, halo, ester, nitro, amino, alkyl, alkoxy and amido.

Deprotecting the diamide diamine intermediate may proceed by forming a solution comprised of the protected diamide diamine intermediate, an alcohol and a hydrazine based reagent, optionally adding a base to the solution, heating the solution to reflux for a period of time sufficient to remove the protective group, filtering a by-product, removing the alcohol, dissolving the residue in water, adjusting the pH to 7 or greater, depending on the hydrazine derivative used, and, extracting the diamide diamine intermediate. A base may optionally be added to the solution where necessary to remove acids that may have been formed by addition of the hydrazine based reagent.

The activated diacid may be selected from the group consisting of oxalate, malonate and succinate activated derivatives.

The activated malonate derivative is selected from the group consisting of disubstituted malonates, monosubstituted malonates and unsubstituted malonates.

The method may further include complexing a transition metal to the deprotonated amides within the macrocycle of the macrocyclic tetraamido compound. The step of complexing the transition metal may include suspending the macrocyclic tetraamido compound in a liquid, deprotonating the amides within the macrocycle of the macrocyclic tetraamido compound with a base, and adding a metal ion. The liquid may be a solvent, such as, for example, THF. The metal ion may be introduced by addition of a metal ion with a halide, a pseudohalide, or displaceable mono-, bi-, tri-, tetra-, penta-, or hexadentate ligands or combinations thereof sufficient to complete the coordination environment of the metal ion. An exemplary displaceable ligand is acetyl acetonate. The metal halide may be selected from the transition metal halides. Iron (III) is a most preferred metal. The base may be an organic soluble or insoluble base, such as those selected from the group consisting of lithium, sodium, or potassium bis-trimethylsilylamide, lithium, sodium, or potassium di-isopropyl amide, t-butyl lithium, n-butyl lithium, phenyl lithium, and lithium or sodium dicyclohexylamide or an inorganic base such as lithium, sodium or potassium hydride.

The method may further include complexing a transition metal to the amides of the macrocyclic tetraamido compound. The step of complexing the transition metal may include suspending the macrocyclic tetraamido compound in a liquid, deprotonating the amides of the macrocyclic tetraamido compound with a base, and adding a metal ion. Complexing may further comprise oxidizing to produce a metal chelate complex. Oxidizing to produce the metal chelate preferably comprises exposure to one of air, oxygen, chlorine, bromine or benzoyl peroxide. The liquid may be a solvent, such as, for example, THF. The metal ion may be introduced by addition of a metal ion with a halide. Iron (II) is a particularly preferred metal.

DETAILED DESCRIPTION OF THE INVENTION

The method of the present invention provides a more efficient way to make macrocyclic tetraamido compounds, such as those having the structure

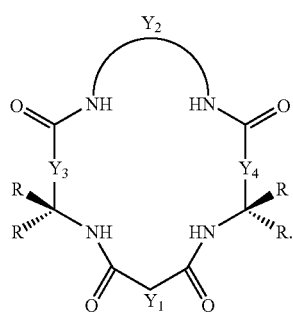

The macrocyclic tetraamido compound may be complexed with a metal, as follows:

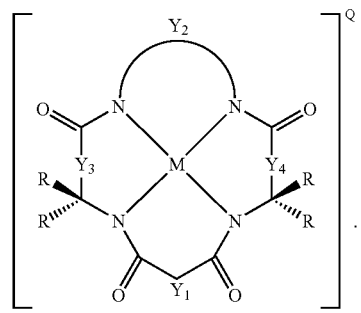

In both of the foregoing structures, $Y_1$, $Y_3$ and $Y_4$ each represents a bridging group, having zero, one, two or three carbon containing nodes for substitution, and $Y_2$ is a bridging group having at least one carbon containing node for substitution. Each node contains a C(R) or a C(R)$_2$ unit and each R substituent is the same or different from the remaining R substituents. Each R substituent (i) is selected from the group consisting of H, alkyl, cycloalkyl, cycloalkenyl, alkenyl, aryl, alkynyl, alkylaryl, halogen, alkoxy, or phenoxy, CH$_2$CF$_3$, CF$_3$ and combinations thereof, or (ii) forms a substituted or unsubstituted benzene ring of which two carbon atoms in the ring form nodes in the Y unit, or (iii) together with a paired R substituent bound to the same carbon atom, forms a cycloalkyl or a cycloalkenyl ring, which may include an atom other than carbon, e.g., cyclopropyl, cyclobutyl, cyclopentyl, or a cyclohexyl ring. M in the second structure is a transition metal with oxidation states of I, II, III, IV, V, VI, VII or VIII, or selected from Groups 3, 4, 5, 6, 7, 8, 9, 10 and 11 of the Periodic Table of the Elements. Q may be any counterion, which would balance the charge of the compound on a stoichiometric basis.

An exemplary compound has the structure:

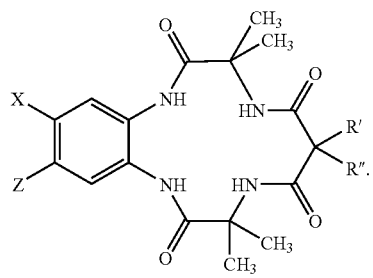

When complexed with a metal, the compound has the structure:

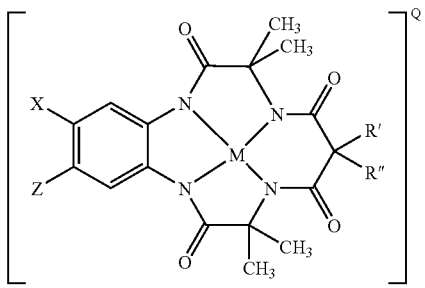

wherein X and Z may be H, electron-donating or electron-withdrawing groups and R' and R" may be any combination of H, alkyl, cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon; M is a transition metal with oxidation states of I, II, III, IV, V, VI, VII or VIII, or selected from Groups 3, 4, 5, 6, 7, 8, 9, 10 and 11 of the Periodic Table of the Elements; Q is any counterion which would balance the charge of the compound on a stoichiometric basis.

The X and Z groups can be H, or either electron donors or electron withdrawing groups. Electron withdrawing groups include halogens, such as Br, I, and, most preferably, Cl$^-$. Further, SO$^-_3$, OSO$_3^-$, OSO$_3$R (R as used in OSO$_3$R being defined, without limitation, as H, alkyl, aryl, alkylaryl) and NO$^-_2$ are appropriate groups. Electron donor groups include alkoxy (without limitation, methoxy, ethoxy, propoxy and butoxy), alkyl (without limitation, methyl, ethyl, propyl, n-butyl and t-butyl) and hydrogen. These groups change the electron density of the metal ligand complex and impact its reactivity.

R' and R" appear to have an impact on the sustained catalytic stability of the macrocyclic tetraamido ligands when used for catalysis. Although each can be individually chosen from H, alkyl, alkenyl, aryl, alkynyl, halogen, alkoxy, or phenoxy substituents, short chain alkyl appears preferred. Especially preferred is when R' and R" are the same and are selected from ethyl and methyl, or when R' and R" combine to form a cycloalkyl or cycloalkenyl ring, especially cyclopropyl, cyclobutyl, cyclopentyl or cyclohexyl. The cycloalkyl ring may include at least one other atom other than carbon, such as, without limitation, N, O, or S. The most preferred and most robust embodiments are those in which R' and R" are the same and are selected from the group consisting of methyl, CF$_3$, hydrogen, halogen and a four membered ring formed together with the carbon atom to which both are bound. These latter groups are either unreactive, form strong bonds with the cyclic carbon, are sterically hindered, and/or are conformationally hindered such that intramolecular oxidative degradation is restricted.

The metal M is a transition metal with oxidation states of I, II, III, IV, V, VI, VII or VIII; or may be selected from Group 3 (Sc, Y, lanthanides and Actinides), Group 4, (Ti, Zr, Hf), Group 5 (V, Nb, Ta), Group 6 (Cr, Mo, W), Group 7 (Mn, Tc, Re), Group 8 (Fe, Ru, Os), Group 9 (Co, Rh, Ir), Group 10 (Ni, Pd, Pt) and Group 11 (Cu, Ag, Au) of the Periodic table of the Elements. It is preferably selected from the group consisting of Sc, Ti, V, Cr, Mn, Fe, Co, Ni, Cu, Zn (Group 12 of the Periodic Table), Mo and W.

Q is any counterion which would balance the charge of the compound on a stoichiometric basis. Both negative and positive counterions may be useful. A generally positively charged counterion is preferably chosen from, but not limited to: alkali metal counterions (e.g., K, Li, Na), [NR*$_4$]$^+$ and [PR*$_4$]$^+$, wherein each R* is individually selected from H, alkyl, aryl, alkylaryl, alkenyl, or can fuse together to form a cycloalkyl or cycloalkenyl or aryl ring which may contain at least one atom other than carbon. A generally negatively charged counterion is preferably chosen from, but not limited to [BF$_4$]$^{-1}$ and [PF$_6$]$^{-1}$.

The metal M, may optionally attach to any labile ligand. These include, preferably, but without limitations, H$_2$O, Cl$^-$, and CN$^-$.

The macrocyclic tetraamido compounds are described in detail in U.S. Pat. Nos. 5,847,120, 5,876,625, 5,853,428, 6,054,580, and 6,136,223, the disclosures of which are hereby incorporated herein by reference. Because of the complex nature of these compounds, within the specification, they are not named, but for convenience are referred to by the substituents present in them. The structure represented above, for example, can be titled 5,6(4,5-Di-X-Benzo)-3,8,11,13-tetraoxo-2,2,9,9-tetramethyl-12,12-diethyl-1,4,7,10-tetraazacyclotridecane (or Tetramethyl diethyl di-X-benzene (TMDE-DXB, where X=Cl, H, Me, OMe)). Thus, for convenience, in the above structure, where there are two methyl groups each on the carbon α to an amide donor of the ligand, and there are two ethyl groups acting as R' and R", the compound is referred to as TMDE-DXB. When R' and R" are methyl groups, the compound is referred to as TMDM-DXB. When the groups X and Z are both chloro, the compound is referred to as TMDE-DCB or TMDM-DCB. A further shortening of the name of the compounds is used throughout where for example TMDE-DCB is referred to as DCB and TMDM-DCB is referred to as DCB*, the * specifically denoting that R' and R" are methyl. Where the transition metal is iron, the compound with Fe(III) and the axial ligand H$_2$O can be referred to herein as [Fe(H$_2$O)DCB]$^-$.

The improved method for synthesizing the macrocyclic tetraamido compounds takes much less time than prior methods. Whereas the prior procedures required a week or longer to complete, the method of the present invention can be completed in three days or less. The method of the present invention allows for the elimination of several isolation steps, thereby significantly saving time, simplifying the procedure, improving yield by avoiding material loss and making it feasible for large-scale commercial production; consequently, significantly reducing the cost of the procedure.

The improved method comprises generally, protecting the amino portion of an amino carboxylic acid to form a protected amino carboxylic acid. Then, the protected amino carboxylic acid is mixed with a solvent. The carboxylic acid portion of the protected amino carboxylic acid is converted to an acid chloride, an acid bromide or an acid iodide to form a protected amino acid halide, which is reacted with a diamine in the presence of another solvent and base to form a protected diamide diamine intermediate. The diamide diamine intermediate is then deprotected and reacted with an activated diacid to form the macrocyclic tetraamido compound. The method may further include complexing the macrocyclic tetraamido compound with a transition metal.

The procedure set forth in Gordon-Wylie et al., U.S. Pat. No. 6,051,704, the disclosure of which is hereby incorporated herein by reference, uses protected and unprotected amino carboxylic acids, diamines and diacids, such as the oxalates and malonates, but reacts them in a different sequence, with different solvents and under different reaction conditions. The '704 patent describes variations in the size of the tetraamido ring structure using a format that will be adopted for purposes of the present application. The following structure is used herein to define the shorthand notation shown in Tables 1 and 3 that specifies the chelate ring sizes (including the metal ion) that are formed when reactants in a given portion of the table are used to form the macrocyclic ligand, as coordinated to a transition metal center.

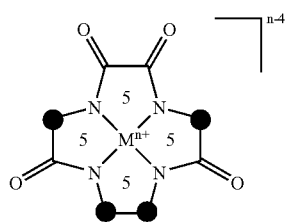

The structure above illustrates a (5,5,5,5) macrocyclic ligand shown in metal coordinated form with chelate ring sizes (including the metal ion) indicated. Using a counter-clockwise rotation, the specific macrocycle employed is 5aa-5ca-5 cc-5ac- (or any cyclic permutation thereof). Amine functionalities are indicated by (a) and carboxylate functionalities are indicated by (c). Six membered rings, might be shown, for example, as 6aa-6ca-6 cc-6ac, and 7 membered rings would have a 7 in front of the letters. As shown in the '704 Patent, combinations of different ring sizes and variations in the order of the amino and carboxylic functionalities within each ring of the macrocyclic ligand can be made. Four, five, six and seven membered rings are preferred, with four, five and six membered rings, and combinations thereof, most preferred.

Information concerning the preparation of the various functional groups that can be used as starting materials for the present invention is available in the literature. One source is R. C. Larock, "Comprehensive Organic Transformations: A Guide to Functional group Preparations," Wiley-VCH, N.Y., pub. ($2^{nd}$ ed., 1999). Agents that will convert carboxylic acids to the activated carboxylic acid derivative form are also described in Larock.

Table 1 identifies some representative α and β amino carboxylic acids of interest for the preparation of macrocyclic tetraamides, either in parent, hidden, or protected/activated forms.

TABLE 1

The Amino Carboxylic Acids
Derivatives of α-Amino Carboxylic Acids (5ac)

| Biological Amino Acids | Derivatives of Biological Amino Acids |
|---|---|
| Glycine | ε-N,N,N-trimethyllysine |
| Alanine | 3-methyl histidine |
| valine (L-α-amino-isovaleric acid) | 5-hydroxy lysine |
| Leucine | O-phosphoserine |
| Isoleucine | γ-carboxyglutamate |
| Methionine | ε-N-acetyllysine |
| Tryptophan | ω-N-methylarginine |
| Serine | Thyroxine |
| Threonine | Ornithine |
| Tyrosine | β-cyanoalanine |
| Cysteine | Homocysteine |
| Lysine | Azaserine |
| Arginine | S-adenosylmethionine |
| Histidine | citrulline |
| asparagine (aspartic acid) | (L-2-amino-5-ureidovaleric acid) |
| glutamine (glutamic acid) | |
| phenylalanine (L-α-amino-β-phenyl propionic acid) | |

Other Amino Acids

| | |
|---|---|
| (S)-2-amino-3-methoxypropionic acid | α-aminohydrocinnamonitrile |
| α-amino-β-methylaminopropionic acid hydrochloride | L-2-amino-4-hydroxy butyric acid |
| R(−)-2-amino-2-methyl butanedioic acid | (R,S)-2-amino-3-hydroxy-3-methyl butanoic acid |
| S(+)-2-amino-2-methyl butanedioic acid | (2S,3R)-2-amino-3-hydroxy-4-methyl pentanoic acid |
| S(+)-2-amino-2-methyl butanoic acid hydrate | DL-α-amino-β-hydroxy-valeric acid |
| 2-amino-2-methyl butyric acid | α-amino-β-imidazole propionic acid |
| 2-amino-3-methyl butyric acid | α-amino-γ-(3-indole) butyric acid |
| 2-amino-2-methyl glutaric acid | α-amino-β-ketoadipic acid methyl ester |
| 2-amino-5-methyl hexanoic acid | α-aminolauric acid |
| R(−)-2-amino-2-methyl-3-hydroxy propanoic acid | 2-amino-malonamide |
| S(+)-2-amino-2-methyl-3-hydroxy propanoic acid | 2-amino-3-mercapto propionic acid |
| 2-amino-7-methyl octanoic acid | (2S,3S)-2-amino-3-methoxy butanoic acid |
| (2S,4S)-2-amino-4-methyl pentanedioic acid | S(−)-2-amino-2-methyl-4-pentenoic acid Monohydrate |
| (S)-2-amino-2-methyl-4-phosphonobutanoic acid | D-2-amino-4-methyl-5-phosphono-3-pentenoic acid |
| DL-2-amino-4(methylsulfonyl)butyric acid | S(−)-2-amino-3-(1-napthyl)propanoic acid |
| D-α-amino-nonylic acid | 2-amino-2-norbornane carboxylic acid |

TABLE 1-continued

The Amino Carboxylic Acids
Derivatives of α-Amino Carboxylic Acids (5ac)

| | |
|---|---|
| (+/−)α,-azelaic acid | 2-aminopelargonic acid |
| α-amino oleic acid | R(−)-α-aminophenyl acetic acid (D(−)-α-phenyl glycine) |
| L-2-amino-4-pentenoic acid (L-C-allyl glycine) | R(−)-2-amino-2-phenylbutyric acid |
| 2-amino-3-phenylbutanoic acid | L-2-amino-3-ureidopropionic acid (albizzin) |
| DL-2-amino-4-phenylbutyric acid | (2R,3S)-2-amino-3-phenylthiobutanoic acid hydrochloride |
| DL-2-aminovaleric acid (DL-norvaline) | L(+)-2-amino-4-phosphonobutyric acid |
| D(−)-2-amino-5-phosphono pentanoic acid (D(−)-2-amino-5-phosphono valeric acid) | L(+)-2-amino-5-phosphono pentanoic acid (L(+)-2-amino-5-phosphono valeric acid) |
| D(−)-2-amino-4-phosphonobutyric acid | cis(+/−)-1-amino-3-phosphono cyclohexane carboxylic acid |
| D(−)-2-amino-3-phosphono propionic acid | trans(+/−)-1-amino-3-phosphono cyclopentane carboxylic acid |
| cis(+/−)-1-amino-3-phosphono cyclopentane carboxylic acid | D(−)-2-amino-6-phosphono hexanoic acid |
| L(+)-2-amino-7-phosphono heptanoic acid | DL-α-amino-hexanoic acid |
| DL-2-amino-8-phosphono octanoic acid | 1-aminocyclopropane-1-carboxylic acid |
| DL-α-amino-2-thiopheneacetic acid | 1-aminocyclobutane-1-carboxylic acid |
| DL-α-amino-3-thiopheneacetic acid | 1-aminocyclopentane-1-carboxylic acid (cycloleucine) |
| 2-amino-4,4,4-trifluorobutyric acid | 1-aminocyclohexane-1-carboxylic acid |
| 2-aminostearic acid | 2-aminodecanoic acid |
| DL-2-amino suberic acid | α-amino succinic acid |
| L(+)-2-amino-6-(O,O'-Diethylphosphono)hexanoic acid | (2S,3S)-2-amino-3-ethoxy butanoic acid hydrochloride |
| L-2-amino-4-sulfamoyl butyric acid | 2-amino-3-fluoro butyric acid |
| L-2-amino-3-sulfamoyl propionic acid | L-α-amino-γ-guanidino butyric acid |
| DL-2-amino-7-sulfoheptanoic acid | L-α-amino-β-guanidino propionic acid |
| D-α-amino adipic acid | 2-amino heptanoic acid |
| L-α-amino adipic acid | 2-amino hexadecanoic acid |
| (+/−)α,δ-diamino-adipic acid | DL-2-amino hexanedioic acid |
| L-α-amino-γ-bromo butyric acid | S(+)-2-amino-2-methyl-3-phenyl propanoic acid |
| α-amino-isobutyric acid (a-methyl alanine) | L-2-amino-4-methyl-5-phosphono-3-pentenoic acid |
| D-α-aminobutyric acid | 2-amino-nonanoic acid |
| L-α-aminobutyric acid | DL-α-amino-octanoic acid (DL-α-aminocaprylic acid) |
| D-2-amino caproic acid | DL-2-amino-4-pentenoic acid (DL-C-allyl glycine) |
| D-α-amino caprylic acid | S(+)-α-aminophenyl acetic acid (L(+)-α-phenyl glycine) |
| L-threo-α-amino-β-chlorobutyric acid | S(+)-2-amino-2-phenylbutyric acid |
| L(+)-2-amino-3-phosphono propionic acid | L-2-aminovaleric acid (L-norvaline) |
| trans(+/−)-1-amino-3-phosphono cyclohexane carboxylic acid | cis-1-amino-3-(2-phosphonoacetyl) cyclobutane-1-carboxylic acid |
| D(−)-2-amino-7-phosphono heptanoic acid | L(+)-2-amino-6-phosphono hexanoic acid |
| DL-α-aminopimelic acid | (+/−)α,γ-diaminoglutaric acid |
| (+/−)α,ω-diaminosuberic acid | |

Derivatives of β-Amino Carboxylic Acids (6ac)

| Registry # | Compound containing 2-amino-benzoic acid |
|---|---|
| 118-92-3 | (o-amino-benzoic acid, anthranilic acid) |
| 619-17-0 | 4-nitro- |
| 616-79-5 | 5-nitro- |
| 4389-45-1 | 3-methyl- |
| 2305-36-4 | 4-methyl- |
| 2941-78-8 | 5-methyl- |
| 4389-50-8 | 6-methyl- |
| 609-86-9 | 3,5-diiodo- |
| 5653-40-7 | 4,5-dimethoxy- |
| 50419-58-4 | 3,4-dimethyl- |
| 14438-32-5 | 3,5-dimethyl- |
| 15540-91-7 | 3,6-dimethyl- |
| 2789-92-6 | 3,5-dichloro- |
| 609-85-8 | 3,5-dibromo- |
| | 3,5-dibromo-6-fluoro- |
| 118-92-3 | (o-amino-benzoic acid, anthranilic acid) |
| 3177-80-8 | 3-methoxy- |
| 6705-03-9 | 5-methoxy- |
| 394-31-0 | 5-hydroxy- |
| 4920-81-4 | 3-hydroxy-hydrochloride |
| 446-32-2 | 4-fluoro- |
| 446-08-2 | 5-fluoro- |
| 434-76-4 | 6-fluoro- |
| | 4-chloro-5-sulfamoyl- |
| 6388-47-2 | 3-chloro- |

-continued

Derivatives of β-Amino Carboxylic Acids (6ac)

| Registry # | |
|---|---|
| 89-77-0 | 4-chloro- |
| 635-21-2 | 5-chloro- |
| 2148-56-3 | 6-chloro- |
| | 3-bromo-5-methyl- |
| 1765-42-0 | 3,4,5,6-tetrafluoro- |
| 61948-85-4 | 3,4,5-trimethoxy- |

| Registry # | Other β-amino carboxylic acids |
|---|---|
| | 3-amino-5-phenylthiophene-carboxamide |
| 5434-20-8 | 3-amino-pthalic acid |
| 627-95-2 | β-amino-valeric acid hydrochloride |
| | 2-amino-4-methyl-thiophene-3-carboxamide |
| | 2-amino-5-methyl-thiophene-3-carboxamide |
| 1068-84-4 | amino-malonic acid |
| 614-19-7 | β-amino-hydrocinnamic acid (D,L-3-amino-3-phenyl-propionic acid) |
| 4507-13-5 | 2-amino-5-ethylthiophene-3-carboxylic acid, ethyl ester |
| 52834-01-2 | 2-amino-4,6-dimethyl-3-pyridinecarboxylic acid hydrochloride |
| 54711-21-6 | 5-amino-4-cyano-1-methyl-pyrazole |
| 698-29-3 | 4-amino-5-cyano-2-methyl pyrimidine |
| | 4-amino-5-cyano-2-methoxy pyrimidine |
| 16750-40-6 | 3-amino-butyronitrile |
| 82-24-6 | 1-aminoanthraquinone-2-carboxylic acid |
| 107-95-9 | 3-amino-propionic acid (β alanine) |
| 41680-34-6 | 3-aminopyrazole-4-carboxylic acid |
| | 2-amino-4,5,6,7-tetrahydrobenzo(b)thiophene-3-carboxylic acid ethyl ester |
| 300-34-5 | 3-amino-L-tyrosine |
| 87550-19-4 | 3,6-dinitrophthalic acid pyridine salt |
| 5959-52-4 | 3-amino-2-napthoic acid |
| 5345-47-1 | 2-amino-nicotinic acid (2-aminopyridine-3-carboxylic acid) |
| 82-24-6 | 1-amino-anthraquinone-2-carboxylic acid |
| 1664-54-6 | 3-amino-3-phenyl-propionic acid |
| 50427-77-5 | 5-amino-1-phenylpyrazole-4-carboxamide |
| 72-40-2 | 5(4)-aminoimidazole-4(5)-carboxamide hydrochloride |
| 2627-69-2 | 5-amino-4-imidazole carboxamide riboside |
| 68302-09-0 | 2-amino-7-ethyl-5-oxo-5H-[1]benzopyrano[2,3-b]pyridine-3-carbonitrile |
| 22603-53-8 | 2-amino-3,5-dinitrobenzonitrile |
| | 5-amino-4-cyano-1-(4-chlorophenyl)pyrazole |
| | 5-amino-4-cyano-1-(4-nitrophenyl)pyrazole |
| 16617-46-2 | 5-amino-4-cyano pyrazole |
| 21112-45-8 | β-amino-crotonic acid |
| 6375-47-9 | 3-amino-4-acetamido anisole |
| 5424-01-1 | 3-amino pyrazine-2-carboxylic acid |
| 10312-55-7 | 2-amino terepthalic acid |
| 868-54-2 | 2-amino-1-propene-1,1,3-tricarbonitrile |
| 584-20-3 | 3-amino-4,4,4-trifluorobutyric acid |

The amino carboxylic acid may be an α spiro-cyclohexyl-, spiro-cyclopentyl-spiro-cyclo-butyl-, or spiro-cyclopropyl-amino carboxylic acid.

In one embodiment of the method, protecting the amino portion of the amino carboxylic acid may be done by reacting a selected one of the foregoing amino carboxylic acids with an anhydride. The anhydride may be one selected from the group consisting of phthalic anhydride, substituted phthalic anhydride, and 2,3-diphenylmaleic anhydride.

Detailed examples of protecting groups may readily be found in T. W. Greene and P. G. M. Wuts, "Protective Groups in Organic Synthesis", John Wiley and Sons, New York (3$^{rd}$ ed., 1999). An extensive list of protecting/activating groups particularly suitable for peptide synthesis may be found in G. A. Fletcher and J. H. Jones, "A List of Amino-Acid Derivatives Which are Useful in Peptide Synthesis", Int. J. Peptide Protein Res. 4, (1972), p. 347–371. Some examples suitable for use in the present invention are shown in Table 2 below.

TABLE 2

| Protected/ Activated Amines | Hidden Amines | Protected/ Activated Carboxylic Acids | Hidden Carboxylic |
|---|---|---|---|
| N-alkyl amines | azides | activated esters | nitriles |
| amides | azo compounds | acyl halides | oxazolines |
| amino acetals | imides | amides | |
| N-benzyls | isocyanates | anhydrides | |
| carbamates | isothiocyanates | hydrazides | |
| enamines | nitrilium ions | O-acyl oximes | |
| hydrazines | nitro compounds | oxazolidines | |
| imines | phosphazos | oxazalones | |
| N-oxides | | phosphite esters | |
| N-phosphinyls | | silyl esters | |
| N-phosphoryls | | stannyl esters | |
| N-Metal derivatives | | substituted benzyl esters | |
| | | substituted ethyl esters | |
| silyl amines (N-Si) | | substituted methyl esters | |
| N-Sulfenyls | | sulfonyl esters | |
| 17sulfonamides | | sulfenyl esters | |
| N-Sulfonyls | | | |
| urea derivatives | | | |

As used herein "parent groups" (shown in *italics* in the heading of Table 2) define a preferred synthetic functionality. "Protected/activated groups" refers to those groups that contain an easily recognizable portion of the parent group. "Hidden groups" as used herein refers to those groups that need not contain an easily recognizable portion of the parent group but which are capable of ready conversion to the parent group or to a protected/activated form of the parent group.

A common protection and deprotection step for amines suitable for use in the present invention is shown schematically in Sequence 1 below.

(a) Protection of an Amine using an Anhydride
(Condensation to Form a Phthalimide)

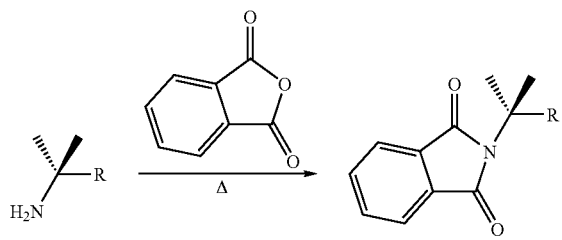

(b) Deprotection of an Amine

Seq. (1)

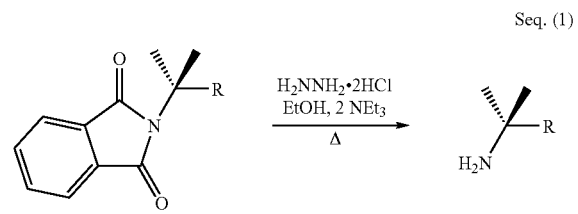

Suitable means for activating a carboxylic acid for reaction with an amine to form an amide are given in Sequences 2 and 3.

Seq. (2)

(a) Activation of a carboxylic acid
(esterification of a carboxylic acid)

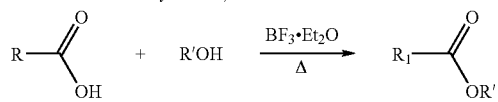

(b) Amide formation

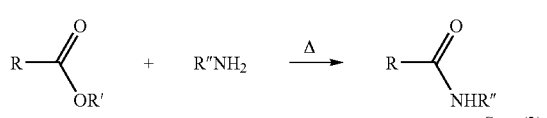

Seq. (3)

(a) Activation of a carboxylic acid

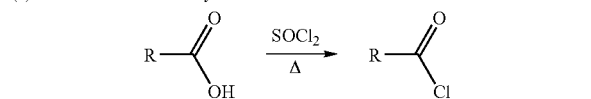

(b) Amide formation

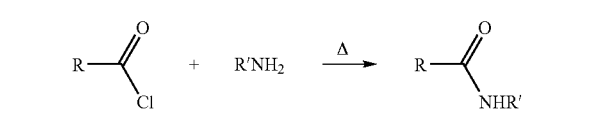

In the method of the invention, the protected amino carboxylic acid is combined with a first solvent. The first solvent is preferably chosen from those hydrocarbon solvents that do not react with agents suitable for forming activated carboxylic acids appropriate for subsequent reaction with an amine to from an amide.

In one embodiment of the method, toluene is chosen as the first solvent. The protected amino carboxylic acid is poured into the toluene. In this embodiment, the second solvent, used in the formation of the diamide diamine, may be THF or a dihaloalkane. The second solvent is used in the presence of a base, such as triethylamine or other tertiary amine or heterocyclic bases like pyridine.

In another embodiment of the method of the invention, the first solvent is a dihaloalkane. In this embodiment, the dihaloalkane is added to the protected amino carboxylic acid. Examples of suitable dihaloalkanes for use as the first and second solvents include 1,2-dichloroethane, dichloromethane, dibromomethane, and 1,2-dibromoethane. In this embodiment, the second solvent, used in the formation of the diamide diamine, may be THF or a dihaloalkane.

After the addition of the first solvent, activation of the carboxylic acid portion of the protected amino carboxylic acid occurs by esterification, as shown schematically above, or by acid halide formation. Activating the carboxylic acid portion of the amino carboxylic acid by esterification may comprise reaction with an ester forming reagent, such as $BF_3 \cdot Et_2O$ and the like.

In acid halide formation, an organic or inorganic acid halide is added to the reaction mixture to convert the protected amino carboxylic acid to a protected amino activated carboxylic acid derivative. The organic or inorganic acid halide may be any one of acid chlorides or acid bromides. Alternatively, $H_2SiI_2$ can be used to form an acid iodide. See, Keinan, E.; Sahai, M. *Journal of Organic Chemistry* 1990, 55, 3922–3926. Those skilled in the art will recognize that other means of acid halide formation will provide an activated carboxylic acid derivative.

In one embodiment, an inorganic acid halide is added to the reaction mixture, which is heated to reflux to convert the protected amino carboxylic acid to a protected amino activated carboxylic acid derivative. Excess inorganic acid halide is partially removed, for example by distillation, from the reaction mixture. The reaction product, protected amino activated carboxylic acid derivative, in this case, a protected amino acid halide, may precipitate upon cooling, preferably to room temperature and below. The precipitate can be filtered and dried. In one embodiment, the inorganic acid halide is thionyl chloride. This step is carried out under dry nitrogen to reduce the chance of hydrolysis of the thionyl chloride.

In the embodiment where the acid halide is thionyl chloride, it is preferably present in amounts ranging from about 0.9 to 1.5 molar equivalents based on amino carboxylic acid. In the different embodiments of the method of the invention, depending on the nature of the first solvent used, the activating agent used to convert the carboxylic portion of the protected amino carboxylic acid to the activated form and the protected amino carboxylic acid are heated to reflux for periods of time ranging from about 1 to about five hours, as needed for the conversion to the protected amino activated carboxylic acid derivative.

The protected amino acid halide is reacted with a diamine in the presence of a second solvent to from a protected diamide diamine intermediate. As stated above, the second solvent, used in the formation of the diamide diamine, may be THF or a dihaloalkane. The diamine may be selected from the group consisting of n,n+1 alkyl diamines, 1,2-aryl diamines, substituted n,n+2 alkyl diamines, substituted o-amino benzylamines and substituted 1,8-diamino napthalenes. The diamine of the method is most preferably selected from the group consisting of substituted and unsubstituted phenylene diamines. The substituted phenylene diamine may be 1,2-amino-4,5-X phenylene, wherein X is selected from the group consisting of H, amino, halo, nitro, alkyl, alkoxy and amido, and 1,2-amino-4-X phenylene, wherein X is selected from the group consisting of H, halo, ester, nitro, amino, alkyl, alkoxy and amido.

Table 3 identifies some representative diamines, of interest for the preparation of macrocyclic tetraamides, either in parent, hidden, or protected/activated forms. Amine and protected/activated or hidden amine functionalities are used interchangeably.

TABLE 3

The Diamines

Derivatives of 1,2-Aryl Diamines (5aa)

| Registry # | Compound containing o-Phenylenediamine |
|---|---|
| | (1,2-Benzenediamine) |
| | No. of Unique Substituents = 1 |
| 18645-88-0 | 3-fluoro- |
| 367-31-7 | 4-fluoro- |
| 153505-39-6 | 3,4-difluoro- |
| 2369-29-1 | 3,5-difluoro- |
| 2369-30-4 | 3,6-difluoro- |
| 76179-40-3 | 4,5-difluoro- |
| 168966-54-9 | 3,4,5-trifluoro- |
| 363-74-6 | 3,4,6-trifluoro- |
| 2993-07-9 | 3,4,5,6-tetrafluoro- |
| 1575-36-6 | 3-bromo- |
| 1575-37-7 | 4-bromo- |
| 1575-38-8 | 3,5-dibromo- |
| 69272-50-0 | 3,6-dibromo- |
| 49764-63-8 | 4,5-dibromo- |
| | No. of Unique Substituents = 2 |
| 75293-95-7 | 4-bromo-5-chloro- |
| 16429-44-0 | 5-bromo-3-chloro- |
| 172215-94-0 | 3-bromo-4,5-dichloro- |
| 98138-54-6 | 4-bromo-3,5-dichloro- |
| 74908-80-8 | 3,5-dibromo-4-chloro- |
| 115440-10-3 | 3-bromo-5-fluoro- |
| 153505-37-4 | 4-bromo-5-fluoro- |
| 153505-35-2 | 3-bromo-4,5-difluoro- |
| 156425-12-6 | 4-bromo-3,5,6-trifluoro- |
| | (1,2-Benzenediamine) |
| | No. of Unique Substituents = 1 |
| 21745-41-5 | 3-chloro- |
| 95-83-0 | 4-chloro- |
| 1668-01-5 | 3,4-dichloro- |
| 5233-04-5 | 3,5-dichloro- |
| 21732-93-4 | 3,6-dichloro- |
| 5348-42-5 | 4,5-dichloro- |
| 30064-28-9 | 3,4,5-trichloro- |
| 1962-10-3 | 3,4,6-trichloro- |
| 877-12-3 | 3,4,5,6-tetrachloro- |
| 34446-43-0 | 3-iodo- |
| 21304-38-1 | 4-iodo- |
| 144793-03-3 | 3,6-diiodo- |
| 76179-43-6 | 4,5-diiodo- |
| | No. of Unique Substituents = 2 |
| 132915-81-2 | 3-chloro-4-fluoro- |
| 153505-33-0 | 3-chloro-5-fluoro- |
| 139512-70-2 | 4-chloro-5-fluoro- |
| 153505-43-2 | 5-chloro-3-iodo- |
| 153505-34-1 | 3-chloro-4,5-difluoro- |
| 170098-84-7 | 4-chloro-3,5-difluoro- |

TABLE 3-continued

The Diamines

| | |
|---|---|
| 156425-14-8 | 4-chloro-3,5,6-trifluoro- |
| 153505-47-6 | 4,5-dichloro-3-iodo- |
| 18225-92-8 | 3,4,6-trichloro-5-fluoro- |
| 153505-45-4 | 5-fluoro-3-iodo- |

| Registry Number | Additional 1,2-Benzenediamines |
|---|---|
| 88580-71-6 | 4,5-dimethyl-<br>4,5-dinitro-<br>4,5-dimethoxy-<br>4,5-diamino-<br>4,5-diacetamido-<br>4,5-ditrifluoromethyl-<br>4,5-dicyano-<br>4,5-dihydroxy<br>4-methyl-<br>4-nitro-<br>4-methoxy-<br>4-amino-<br>4-acetamido-<br>4-trifluoromethyl-<br>4-cyano- |
| 615-72-5 | 4-hydroxy (3,4-diamino-phenol) |
| 59649-56-8 | 3-hydroxy (2,3-diamino-phenol) |

| | Other n,n + 1-Diamines |
|---|---|
| 107-15-3 | ethylene diamine (1,2-diaminoethane) |
| | 1,1,2,2-tetramethyl ethylene diamine |
| 7598-26-7 | 2-amino-3-nitro-5-methyl pyridine |
| 6635-86-5 | 2-amino-3-nitro-4-picoline (2-amino-4-methyl-3-nitro pyridine) |
| 82039-90-5 | 5-amino-4-nitro-imidazole |
| | 5-amino-3-methyl-4-nitro-isoxazole |
| | 5-amino-1,3-dimethyl-4-nitro-pyrazole |
| 6632-68-4 | 6-amino-1,3-dimethyl-5-nitroso-uracil |
| 22603-53-8 | 2-amino-3,5-dinitro-benzonitrile |
| 3531-19-9 | 1-amino-2,4-dinitro-6-chlorobenzene |
| 5442-24-0 | 4-amino-2,6-dihydroxy-5-nitro-pyrimidine |
| | 4-amino-2,6-diketo-1,3-dimethyl-5-nitroso-pyrimidine |
| 1436-59-5 | 1,2-dinitro-tetramethyl-benzene |
| | cis-1,2-diamino-cyclohexane |
| | cis-1,2-diamino-cyclopentane |
| | cis-1,2-diamino-1,2-dimethyl-cyclohexane |
| | cis-1,2-diamino-1,2-dimethyl-cyclopentane |
| 36023-58-2 | 5,6-diamino-2,3-dicyano-pyrazine |
| 5440-00-6 | 5,6-diamino-1,3-dimethyl-uracil |
| | 5,6-diamino-3-methyl-uracil |
| 1758-68-5 | 1,2-diaminoanthraquinone |
| 6968-22-5 | 3-amino-4-nitro-benzoic acid |
| 452-58-4 | 2,3-diamino pyridine |
| 54-96-6 | 3,4-diamino pyridine |
| | 2-amino-3-nitro-5-bromo-pyridine |
| | 4-amino-5-nitro-6-chlor-pyrimidine |
| | 2-amino-3-nitro-9-fluorenone |
| 7598-26-7 | 2-amino-3-nitro-5-methyl-pyridine |
| | 4-amino-5-nitroso-uracil |
| 1672-48-6 | 6-amino-5-nitroso-2-thio-uracil |
| | 2-amino-5-bromo-3-nitro-pyridine |
| 33685-60-8 | 9,10-dinitro-anthracene |
| | 6,7-dinitro-2,3-diphenoxy-quinoxaline |
| 35975-00-9 | 5-amino-6-nitro-quinoline |
| 771-97-1 | 2,3-diamino-napthalene |
| 938-25-0 | 1,2-diamino-napthalene |

TABLE 3-continued

| The Diamines | |
|---|---|
| 39070-63-8 | 3,4-diamino-benzophenone |
| 68836-13-5 | 6,7-dinitro-quinoxaline |
| | 5,6-dinitro-quinoxaline-2,3-dione |
| 2379-57-9 | 6,7-dinitro-quinoxaline-2,3-dione |
| 52057-97-3 | 3,4-diamino-5-hydroxy-pyrazole sulfate |
| 1672-50-0 | 4,5-diamino-6-hydroxy-pyrimidine |
| 13754-19-3 | 4,5-diamino-pyrimidine |
| 3240-72-0 | 4,5-diamino-uracil (5,6-diamino-uracil) |

| Derivatives of n,n + 2 Diamines (6aa) | |
|---|---|
| Registry # | n,n + 2-diamines |
| 4403-69-4 | 2-amino-benzylamine |
| | 2-amino-2-(2-aminophenyl)-propane |
| 109-76-2 | 1,3-diaminopropane |
| 3385-21-5 | 1,3-diaminocyclohexane |
| | 1,3-diamino-1,3-dimethylcyclohexane |
| | 2,4-diamino-2,4-dimethyl-pentane-3-one |
| | 2,4-diamino-2,4-dimethyl-pentane |
| 479-27-6 | 1,8-diaminonapthalene |
| 589-37-7 | 1,3-diaminopentane |
| 7328-91-8 | 1,3-diamino-2,2-dimethyl propane |

The list of n,n+2-Diamines is significantly shorter than for the other derivatives, in large part because the syntheses of the required n,n+2 diamines are more complex than for the n,n+1 diamines.

In order to effectively discuss substitutions at all of the variable positions simultaneously, as in a substituted macrocyclic tetraamide compound, a sum over all of the possible combinations of the basic structural units may be constructed. This type of sum approach (a form of combinatorial analysis) provides a powerful method for the enumeration of all of the possible substituted macrocycles that can be constructed from any given list of substituted starting materials, selected, for instance, from the lists previously cited. While extensive, the foregoing lists are not the only starting materials that can be used in the method of the present invention to synthesize various macrocyclic tetraamido compounds. Those skilled in the art will recognize that other starting materials falling within the general classes of starting materials identified herein may be used. Reference is made to the several literature references cited here, and incorporated herein by reference. For example, the pyridine diamines can also be utilized.

Amino pendant structures are also of considerable interest because they permit the macrocyclic compound or metallocomplex to be tethered to a support, such as a polymer or sand, or to other molecules or substrates having functional groups that will covalently bond with the amine. Groups that covalently bond with amines are well known in the art and include in complexed form, for example, alkyl amines, amides, sulphonamides, imines, and other hidden or protected/activated forms, see Table 2.

The protected diamide diamine intermediate is then deprotected to form a diamide diamine intermediate. Deprotecting the diamide diamine intermediate may proceed, for example, by forming a solution comprised of the protected diamide diamine intermediate, alcohol, such as absolute ethanol, and a hydrazine based reagent, such as hydrazine dihydrochloride. A base may be additionally added for some hydrazine based reagents, but is not necessary for all. The solution is heated to reflux for a period of time sufficient to remove the protective group. The alcohol is removed and the pH is adjusted to 7 or greater, depending on the hydrazine based reagent used, and preferably greater than or equal to 10. Where hydrazine hydrate is added, for example, no additional base is needed. For hydrazine based reagents, such as hydrazine dihydrochloride or hydrazine acetate, for example, a pH of 10 or greater is desirable. The diamide diamine intermediate is extracted.

In the next step, the diamide diamine intermediate is reacted with an activated diacid to form the macrocyclic tetraamido compound of the invention. The activated diacid may be selected from the group consisting of activated oxalate, malonate and succinate and activated derivatives thereof. Activated, as used herein, shall refer to a carboxylic acid derivative that reacts with a primary amine to form a secondary amide.

The activated malonate derivative is selected from the group consisting of disubstituted malonates, monosubstituted malonates and unsubstituted malonates.

Table 4 identifies some representative dicarboxylic acid malonate or oxalate derivatives.

TABLE 4

| The Oxalates and Malonates | | | | |
|---|---|---|---|---|
| Oxalates: Derivatives of Oxalic Acid (5cc) | | | | |
| Registry # | | Compound Name | | |
| | | Oxalyl Chloride | | |
| Malonates: Derivatives of Malonic Acid (6cc) | | | | |
| Registry # | Compound Name | | Registry | Compound Name |
| Disubstituted malonates | | | | |
| 31696-00-1 | Diethyl | butylethylmalonate | | Diethyl di-n-octylmalonate |
| 00596-76-9 | Diethyl | butylhexylmalonate | 24251-93-2 | Diethyl di-n-pentylmalonate |
| 00083-27-2 | Diethyl | butylmethylmalonate | | Diethyl di-2-propenyl malonate |
| | Diethyl | butylethylmalonate | 03195-24-2 | Diethyl di-n- |

TABLE 4-continued

The Oxalates and Malonates

| | | | | | |
|---|---|---|---|---|---|
| | Diethyl | butylpentylmalonate | | Diethyl | propylmalonate |
| | Diethyl | butylpropylmalonate | | Diethyl | ethylheptyl malonate |
| | | "2,2-Diethylbutyric acid" | 00133-13-1 | Diethyl | ethylhexyl-malonate |
| 18719-43-2 | Diethyl | "1,1-cyclobutane dicarboxylate" | | Diethyl | ethyl(1-methyl-butyl) malonate |
| 53608-93-8 | Diethyl | "1,1-cyclopropane dicarboxylate" | 02049-70-9 | Diethyl | ethylmethyl-malonate |
| 01559-02-0 | Diethyl | decylethylmalonate | | Diethyl | ethyl(1-methyl propyl) malonate |
| 05077-96-3 | Diethyl | decylmethylmalonate | 05408-35-5 | Diethyl | ethylnonyl-malonate |
| | Diethyl | diallylmalonate | 00076-67-5 | Diethyl | ethyloctyl-malonate |
| 03195-24-2 | Diethyl | dibenzylmalonate | | Diethyl | ethylpentyl-malonate |
| 00597-55-7 | Diethyl | di-n-butylmalonate | 71691-56-0 | Diethyl | ethylphenyl-malonate |
| 00596-75-8 | Diethyl | di-n-decylmalonate | | Diethyl | ethylpropyl-malonate |
| | Diethyl | diethylmalonate | | Diethyl | methyl(2-methyl butyl) malonate |
| | Diethyl | di-n-heptylmalonate | 34009-61-5 | Diethyl | methyl(2-methyl propyl) malonate |
| | Diethyl | di-n-hexylmalonate | 01575-67-3 | Diethyl | methylnonyl-malonate |
| | Diethyl | dimethylmalonate | 58447-69-1 | Diethyl | methylphenyl-malonate |
| 01619-62-1 | Diethyl | di-n-nonylmalonate | 00083-27-2 | Diethyl | methylpropyl-malonate |
| | | "1,1-cyclopropane dicarboxylate" | | | methyl-iso-propylmalonate |
| | | "1,1-cyclopentane dicarboxylate" | | | "1,1-cyclobutane dicarboxylate" |
| | | ditrifluoromethyl malonic acid | | | "1,1-cyclohexane dicarboxylate" |
| | | difluoro malonic acid | | | ditrifluoroethyl malonic acid |
| | | | | | dichloro malonic acid |

Monosubstituted malonates

| | | | | | |
|---|---|---|---|---|---|
| | Diethyl | amylmalonate | 05398-10-7 | Diethyl | 5-hexenylmalonate |
| J6065-S9-4 | Diethyl | iso-amylmalonate | 10297-07-1 | Diethyl | n-hexylmalonate |
| 05398-08-3 | Diethyl | sec-amylmalonate | 05398-08-3 | Diethyl | 5-hexynylmalonate |
| 00117-47-5 | Diethyl | benzalmalonate | | Diethyl | iso-amylmalonate |
| 05292-53-5 | Diethyl | benzylidenemalonate | 05398-08-3 | Diethyl | iso-butylmethyl malonate |
| 05292-53-5 | Diethyl | benzylmalonate | 06802-75-1 | Diethyl | iso-pentylmalonate |
| 00607-81-8 | Diethyl | 2-benzylsuccinate | 00759-36-4 | Diethyl | iso-propylidene malonate |
| | Diethyl | (4-bromobutyl)malonate | *58447-69-1 | Diethyl | iso-propylmalonate |
| 26971-92-6 | Diethyl | (2-bromoethyl)malonate | 00105-53-3 | Diethyl | isopropylmethyl malonate |
| 18721-64-7 | Diethyl | (7-bromoheptyl) malonate | 06335-37-1 | Diethyl | 4-methoxybenzal malonate |
| | Diethyl | (6-bromohexyl) malonate | 00117-47-5 | Diethyl | 4-methoxybenzyl malonate |
| 29237-82-9 | Diethyl | (5-bromopentyl) malonate | | Diethyl | (1-methylbutyl) malonate |
| 01906-95-2 | Diethyl | (3-bromopropyl) malonate | 05398-08-3 | Diethyl | (2-methylbutyl) malonate |
| 10149-21-0 | Diethyl | 3-butenylmalonate | | Diethyl | (3-methylbutyl) malonate |
| | Diethyl | butylmalonate | 00609-08-5 | Diethyl | (1-methylhexyl) malonate |
| 00133-08-4 | Diethyl | (2-butyl)malonate | 14251-43-5 | Diethyl | methylmalonate |
| *00083-27-2 | Diethyl | iso-butylmalonate | 55898-43-6 | Diethyl | (2-methyl-2-propenyl) malonate |
| *10203-58-4 | Diethyl | sec-butylmalonate | 10203-58-4 | Diethyl | (1-methylpropyl) malonate |
| 00813-58-1 | Diethyl | (3-chloropropyl) malonate | 52180-01-5 | Diethyl | (2-methylpropyl) malonate |
| 03779-29-1 | Diethyl | 2-cyclopenten-1-yl malonate | 01472-85-1 | Diethyl | n-nonylmalonate |
| | Diethyl | n-decylmalonate | 01582-05-4 | Diethyl | n-octylmalonate |

TABLE 4-continued

The Oxalates and Malonates

| | | | | | |
|---|---|---|---|---|---|
| 00077-25-8 | Diethyl | "(3,4-difluoro benzyl) malonate" | 04475-07-4 | Diethyl | "(2,3,4,5,6-penta fluorobenzyl) malonate" |
| | Diethyl | "2-(3,3-dimethyl butyl) malonate" | 06065-59-4 | Diethyl | 4-pentenylmalonate |
| 06065-63-0 | Diethyl | n-dodecylmalonate | | Diethyl | n-pentylmalonate |
| 07252-87-1 | Diethyl | (2-ethylbutyl)malonate | | Diethyl | iso-pentylmalonate |
| 25234-24-6 | Diethyl | ethylidenemalonate | 06628-68-8 | Diethyl | 2-pentylmalonate |
| 01462-12-0 | Diethyl | ethylmalonate | 02163-48-6 | Diethyl | (2-phenylethyl) malonate |
| | Diethyl | (1-ethylpropyl) malonate | | Diethyl | propylmalonate |
| 00685-88-1 | Diethyl | (4-fluorobenzyl) malonate | | Diethyl | iso-propylmalonate |
| 00607-83-0 | Diethyl | fluoromalonate | | Diethyl | (3-trifluoromethyl benzyl)malonate |
| 41433-81-2 | Diethyl | n-heptylmalonate | 22390-04-1 | Diethyl | undecylmalonate |
| 69298-59-5 | Diethyl | n-hexadecylmalonate | 1068-84-4 | | amino-malonic acid |

Unsubstituted Malonates 06768-23-6 Diethyl malonate

A route for the preparation of substituted and unsubstituted malonates has been reported by A. P. Krapcho, E. G. E. Jahngen, Jr. and D. S. Kashdan, "α-carbalkoxylations of carboxylic acids. A general synthetic route to monoesters of malonic acids," Tet. Lett. 32, p.2721–2723 (1974). Additional substituted malonic acids that would be useful as diacids in the method of the present invention are disclosed in U.S. Pat. No. 6,297,400 B1, the relevant portions of which are hereby incorporated herein by reference.

Procedures for Preparing Several Malonyl Dihalides Follow.

Synthesis of Difluoromalonyl Dichloride

The synthesis was performed following a literature method Buschmann, J.: Lentz, D., Luger, P.; Roettger, M.; Oberhammer, H. *Journal of Physical Chemistry A* 2000, 104, 7123–7128, with minor modifications. Sodium difluoromalonate was prepared by alkaline hydrolysis of diethyl difluoromalonate. In the next step phosphoryl chloride was used to convert sodium difluoromalonate to difluoromalonyl dichloride.

Sodium Difluoromalonate

Sodium hydroxide (0.90 g, 0.022 mol) was dissolved in 5 mL water followed by dilution with 25 mL ethanol and the solution was heated to 60° C. Diethyl difluoromalonate (2 g, 0.01 mol) was then added to the stirred reaction mixture. A white precipitate formed immediately. The mixture was stirred for another 45 min while maintaining the temperature at 60° C. The fine white precipitate was collected and dried at 45° C. for 18 h. Yield 1.84 g (99%).

Difluoromalonyl Dichloride

Sodium difluoromalonate (1 g, 0.005 mol) was taken with phosphoryl chloride (1.8 ml) and slowly heated up to 90° C. After stirring the reaction mixture for 2 h approximately 0.6 mL of liquid from the reaction mixture was vacuum distilled at 25° C. into a trap at −196° C. The acid chloride was used for ligand synthesis without further purification.

Cyclopropylmalonyl Dichloride

The cyclopropylmalonyl dichloride was prepared according to the procedure set forth in Black, D. S. C., Blatt, H., Vanderzalm, C. H. B., and Liepa, A. J., *Australian Journal of Chemistry* 1983, 36, 1133–1140.

Cyclobutylmalonyl Dichloride 1,1-cyclobutylcarboxylic acid (10.021 g, 0.070 mol), 1 drop triethylamine and a stir bar were placed in a round bottom flask. The flask was fitted with a reflux condenser and an $N_2$ atmosphere established. Oxalyl chloride (18.2 ml, 0.210) was added and the mixture was stirred for 5 days at 55° C. Excess oxalyl chloride was removed in vacuo at room temperature to yield the cyclobutylmalonyl dichloride (11.314 g, 97%). The product was not purified.

After the macrocyclic tetraamido compound has been synthesized, it may be complexed with a metal, preferably a transition metal selected from Groups 3, 4, 5, 6, 7, 8, 9, 10, 11, or 12 of the Periodic table of the Elements, discussed above. Complexing may be done by adding to the macrocyclic tetraamido compound under anhydrous conditions, a metal ion with halide, a pseudohalide, or displaceable mono-, bi-, tri-, tetra-, penta-, or hexadentate ligands or combinations thereof sufficient to complete the coordination environment of the metal ion, a solvent and a base. The solvent may be, for example, THF. The metal ion may be selected from the transition metal ions. An exemplary metal is Fe(III). The base may an organic soluble or insoluble base, such as those selected from the group consisting of lithium, sodium, or potassium bis-trimethylsilylamide, lithium, sodium or potassium di-isopropyl amide, t-butyl lithium, n-butyl lithium, phenyl lithium, and lithium or sodium dicyclohexylamide or an inorganic base such as lithium, sodium or potassium hydride.

A particularly useful method includes suspending the macrocyclic tetraamido compound in a liquid, such as THF, deprotonating the amides within the macrocycle of the macrocyclic tetraamido compound with a base, and adding a metal ion. A further step includes oxidizing to produce the metal chelate. Oxidizing preferably comprises adding an oxidizing agent, which may be at least one of air, oxygen, chlorine, bromine or benzoyl peroxide. An exemplary metal is Fe(II).

Experimental

Mass Spectrometry. Electrospray ionization mass spectra were acquired on a THERMO-FINNIGAN-LCQ (San Jose, Calif.) mass spectrometer. Electrospray voltages of 4000–5000 V were utilized. Samples were dissolved in either acetonitrile or dichloromethane at concentrations of approximately 10 pmol/ml and were introduced into the ESI interface prior to data acquisition by direct infusion at a flow rate of 5 μl/min and were introduced prior to data acquisition.

Spectroscopic Methods. 300 MHz $^1$H NMR spectra and 75 MHz $^{13}$C NMR spectra were obtained on an IBM AF300 instrument using an OXFORD Superconducting magnet system, data acquisition was controlled by Tecmag software. Infrared spectra were obtained on a MATTSON GALAXY Series 5000 FTIR spectrometer. UV/vis spectra were obtained on a HEWLETT PACKARD 8452A or 8453 spectrophotometer.

Steps I–III of the method, without isolation of any intermediates, were carried out in 1,2-dichloroethane as the first solvent. The main advantages of using the dihaloalkanes are: 1) the phthalimido protected amino acid is soluble in 1,2-dichloroethane, 2) the thionyl chloride (SOCl$_2$) reaction proceeds more smoothly, 3) close to stoichiometric amounts of SOCl$_2$ can be used with good conversion within a period of time much shorter than heretofore possible with prior art methods, and 4) formation of the phthalimido protected diamide diamine does not form the thick paste that it does, for example, in a toluene/THF mixture (the triethylammonium hydrochloride [Et$_3$NH]Cl is partially soluble in 1,2-dichlorethane).

Procedure A: Synthesis of Phthalimido-Protected Diamide Diamine

The reaction sequence using the dihaloalkane as the first and second solvents in the method is shown below.

anhydride begins to sublime. When 115° C. is reached the solids begin to liquify and this is complete at ~125° C. Condensation begins to appear at ~150° C. and by 155° C. the reaction mixture is clear. Some phthalic anhydride sublimed and adhered to the flask walls but most was washed down the walls by the water during the reaction. The reaction was allowed to proceed until approximately 10 min. after water evolution appeared to cease. The final bath temperature was 190° C. The flask was removed from the oil bath. A condenser and nitrogen adapter were rapidly attached to the flask. A flow of N$_2$ was established over liquid. When the temperature of the liquid reached approximately 140° C., 300 mL of 1,2-dichloroethane was added rapidly. There was an initial boiling of the solvent, but this quickly subsided and the solution temperature dropped to nearly room temperature after all of the 1,2-dichloroethane had been added. Stoppers were placed in the third and fourth necks of the flask. The solution was allowed to cool to room temperature. There was a small amount of solid present. This is a cyclic dimer that forms when the amino carboxylic acid condenses with itself and possibly phthalic anhydride/phthalic acid.

II. Synthesis of a Protected Phthalimidopropanoic Chloride

One of the stoppers was removed and 25.8 mL (0.35 mol) of thionyl chloride (SOCl$_2$) was added, based on the assumption that 10% of the product was the cyclic dimer. The solution was heated to reflux for 4.5 hrs. Gas evolution appeared to cease after 3 hrs. The solution was cooled to

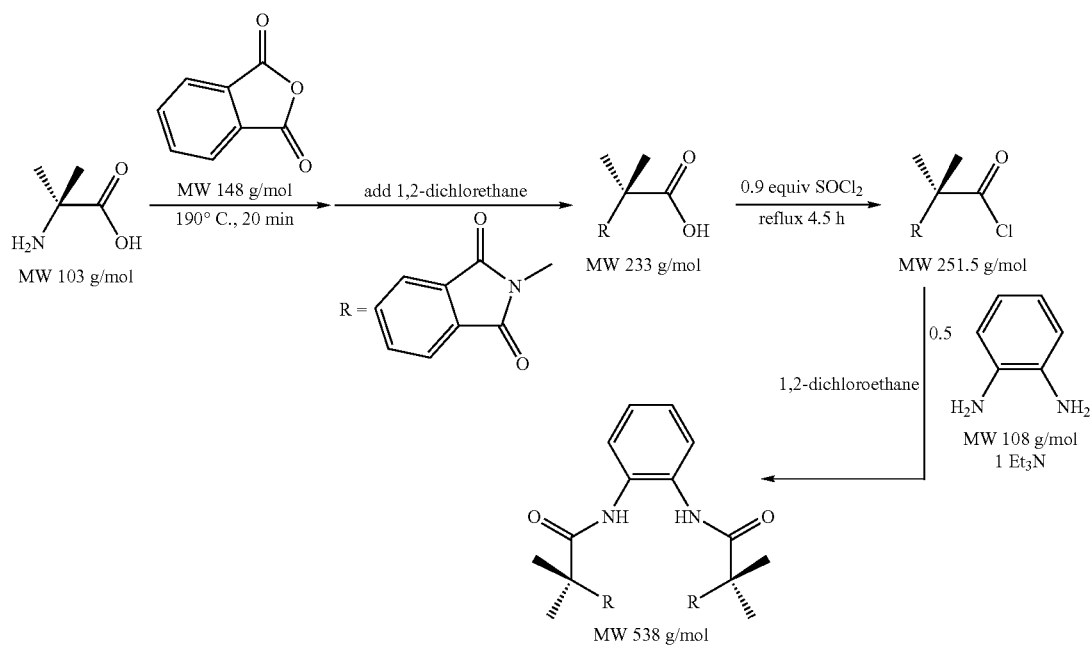

I. Synthesis of a Protected Phthalimidopropanoic Acid

The following is a modification of a procedure described in J. Chem. Soc. Perkin I 1985, 1645.

A 40.4 g (0.39 mol) sample of 2-aminoisobutyric acid and 58.2 g (0.39 mol) phthalic anhydride were combined in a 1000 mL round bottom flask (four necked) containing a stir bar. The flask was placed in an oil bath that had been heated to 175° C. Internal temperatures were monitored and the following observations were made: At ~80° C. phthalic room temperature and filtered to remove solids ($^1$H NMR showed this to be the cyclic dimer, 5.4 g).

III. Synthesis of N,N'-1,2-phenylenebis[2-methyl-2-phthalimidopropanamide], a Protected Diamide Diamine The filtrate was transferred to a 3-neck flask containing a stir bar. The flask was outfitted with a condenser, N$_2$ adapter, and an addition funnel.

A 1,2 dichloroethane solution, 150 mL, containing 1,2-phenylenediamine (21.2 g, 0.2 mol) and triethylamine (NEt$_3$) (54.5 mL, 0.39 mol) was prepared and placed in the addition funnel. The 1,2-phenylenediamine had been recrystallized from ethanol (EtOH), dried, and ground into a powder. This compound can be difficult to dissolve if it is not ground into a powder. The 1,2-phenylenediamine/NEt$_3$ solution was added dropwise to the phthalimido protected amino acid chloride over an approximately 1 hr period under an N$_2$ atmosphere. It is believed that the N$_2$ atmosphere was unnecessary, but used in the interest of caution. Some solid appeared and the solution warmed during the addition. The solution was refluxed overnight. The reaction mixture was cooled in a chilled water bath resulting in the precipitation of a large quantity of solid. 250 mL of water was added to the 1,2-dichloroethane and the mixture was stirred for 5 min. The slurry was filtered, the precipitate was washed with ethanol, which removed a yellow material and then dried in vacuo. 79 g of product was recovered, 83% yield based on the quantity of SOCl$_2$ used. The $^1$H NMR spectrum shows a pure product with the possibility of 0.5–1 equiv of 1,2-dichloroethane present. $^1$H NMR (d$_6$ DMSO) 9.4 (s, 2H), 7.8–7.7 (m, 8H), 7.51–7.49 (m, 2H), 7.16–7.13 (m, 2H), 3.9 (s, 2H {1,2-dichloroethane}, 1.72 (s, 12H).

The overall >80% yield of phthalimido protected diamide diamine is significantly better than the ~55% isolated yield from prior art methods of synthesis, and the time and chemical savings are significant.

The deprotection of the diamide diamine and the formation of the macrocyclic tetraamido compound proceeds as set forth in Procedure C below The embodiment of the method of the present invention using toluene as the first solvent is shown schematically below.

comparison purposes. The most critical aspect of the chemistry in this embodiment appears to be removal of SOCl$_2$ following conversion of the phthalimido protected amino acid to the phthalimido protected amino acid chloride, in Step II. If SOCl$_2$ is not removed, it negatively impacts formation of the phthalimido protected diamide diamine in Step III. A yield of >70% of phthalimido protected diamide diamine has been achieved, based on the quantity of starting 2-aminoisobutyric acid, when the SOCl$_2$ was completely removed and <50% yield when a substantial portion (80–90%) of the excess SOCl$_2$ was estimated to have been removed by distillation (not fractional distillation). 1.5 equiv of SOCl$_2$ for the conversion in Step II appears to be optimal, but variation can be tolerated. Fractional distillation combined with a partial strip of the toluene is expected to remove the vast majority of any unreacted SOCl$_2$ and improve the yield.

The overall >70% yield of phthalimido protected diamide diamine is significantly better than the ~55% isolated yield from prior art methods of synthesis, and the time and chemical savings are significant.

I. Synthesis of a Protected Phthalimidopropanoic Acid 20 g (0.19 mol) of 2-aminoisobutyric acid and 29 g (0.20 mol) phthalic anhydride were combined in a 500 mL round bottom flask containing a stir bar. The flask was placed in an oil bath that had been heated to 130° C. and then the temperature was raised to 195° C. (one trial showed that heating to 175° C. was sufficient for conversion to the desired product). Internal temperatures were monitored and the following observations were made: At ~80° C. phthalic anhydride begins to sublime. When 115° C. is reached the

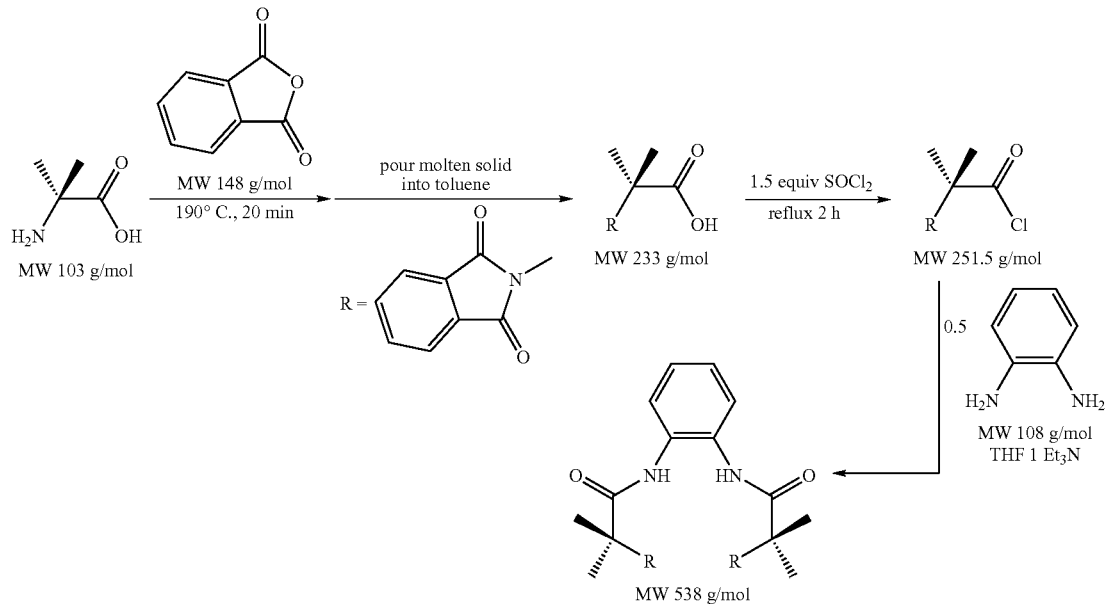

Procedure B: Synthesis N,N'-1,2-phenylenebis[2-methyl-2-phalimidopropanamide], a Phthalimido-protected Diamide Diamine A full run through of the combined Steps I–III without isolation of any intermediates has been done. Syntheses where intermediates have been isolated and quantified have also been done, and then added back into reactions for yield solids begin to liquify and this is complete at ~125° C. Condensation begins to appear at ~150° C. and by 155° C. the reaction mixture is clear. Some phthalic anhydride sublimed and adhered to the flask walls but most was washed down the walls by the water during the reaction. The reaction was taken to ~190° C. for 10 min and then the molten reaction mixture was poured directly into a 1000 mL round bottom flask containing 200 mL of stirred toluene. After approximately 5 min a white precipitate formed. With this volume of toluene only a slight temperature rise was observed.

II. Synthesis of a Protected Phthalimidopropanoic Chloride

The flask containing the phthalimido protected amino acid was placed under inert atmosphere fitted with a reflux condenser and then 25 mL (0.34 mol) of $SOCl_2$ was added. The reaction mixture was heated to reflux, a $NaHCO_3$ solution (1 mol) was used to neutralize the evolved gases. After attaining reflux, gas evolution was vigorous for approximately 20 min and then it slowed noticeably. Most of the solid dissolved during the reaction, 120 min total reaction time, and the solution became pale yellow. The excess $SOCl_2$ and most of the toluene were removed and the solution was filtered to remove the cyclic dimer of the amino acid (2 g, 14 mmol). The remainder of the toluene was removed leaving 42 g (0.17 mol) of phthalimido protected amino acid chloride, yield >85% based on starting 2-aminoisobutyric acid. $^1H$ NMR ($d_6$ DMSO) 7.83 (s, 4H), 1.70 (s, 6H).

III. Synthesis of N,N'-1,2-phenylenebis[2-methyl-2-phalimidopropanamide], a Protected Diamide Diamine The phthalimido protected amino acid chloride was converted to the phthalimido protected diamide diamine in the following manner. A solution of 1,2-phenylenediamine, 10.7 g (0.099 mol) and 27.1 ml $NEt_3$ (0.195 mol) was prepared in 60 mL dry THF. This solution was added drop wise to a 250 mL toluene solution of the phthalimido protected amino acid chloride over a period of 180 min. A large amount of white precipitate formed during the reaction. It was necessary to add 500 mL more toluene during the 1,2-phenylenediamine/$NEt_3$ addition to aid stirring the slurry. The slurry was refluxed overnight, but it is believed that it is not necessary for the reflux to be this long. The slurry was then cooled to room temperature, 250 mL of water was added and then the slurry filtered. The filter cake was washed with 2-propanol and the solid dried in vacuo. Isolated yield: 36 g (0.067 mol). The yield is 70% based on starting amino acid and 80% based on the 42 g of protected amino acid chloride from above. $^1H$ NMR ($d_6$ DMSO) 9.4 (s, 2H), 7.8–7.7 (m, 8H), 7.51–7.49 (m, 2H), 7.16–7.13 (m, 2H), 3.9 (s, 2H {1,2-dichloroethane}, 1.72 (s, 12H).

Alternative Step II of Procedure B

The flask containing the phthalimido protected amino acid was placed under inert atmosphere fitted with a reflux condenser and then 25 mL (0.34 mol) of $SOCl_2$ was added. The reaction mixture was heated to reflux, a $NaHCO_3$ solution (1 mol) was used to trap the evolved gases. After attaining reflux, gas evolution was vigorous for approximately 20 min and then it slowed noticeably. Most of the solid dissolved during the reaction, 120 min total reaction time, and the solution became pale yellow. Approximately 35 mL of toluene/$SOCl_2$ were distilled from the reaction mixture after the 120 min reflux and then the solution was filtered using inert atmosphere techniques to remove the cyclic dimer of the amino acid. No additional workup was performed.

Alternative Step III of Procedure B

The phthalimido protected amino acid chloride from Alternative Step II above was converted to the phthalimido protected diamide diamine in the following manner. A solution of 1,2-phenylenediamine, 4.2 g (0.039 mol) and 10.8 ml $NEt_3$ (0.08 mol) was prepared in 100 mL THF. This solution was added drop wise to the toluene solution of the phthalimido protected amino acid chloride over a period of 180 min. During the addition of the first 20–30 mL of the THF solution of 1,2-phenylenediamine/$NEt_3$ a white "smoke" was observed. It is likely that not all of the $SOCl_2$ was removed in Step II and the $NEt_3$ was reacting with the $SOCl_2$. A white solid also formed during the addition. After all of the THF solution had been added, the slurry was refluxed overnight and then cooled to room temperature. Water, 250 mL, was added to the slurry and then filtered. The filter cake was washed with 2-propanol which removed some brown color and then this solid was dried in vacuo. Isolated yield: 24 g (0.045 mmol). The yield is 47% based on starting amino acid. $^1H$ NMR ($d_6$ DMSO) 9.4 (s, 2H), 7.8–7.7 (m, 8H), 7.51–7.49 (m, 2H), 7.16–7.13 (m, 2H), 1.72 (s, 12H).

The foregoing step III of procedure B was also run using 3,4-diaminobenzoic acid methyl ester, and 4-nitro-1,2-phenylenediamine in place of the 1,2-phenylenediamine. The following steps were carried out for the corresponding protected diamide diamine, protected ester-diamide diamine, and protected nitro-diamide diamine.

The deprotection of any of the protected diamide diamines and the formation of the macrocyclic tetraamido compound proceeds as set forth below.

IV. Synthesis N,N'-1,2-phenylenebis[2-methyl-2-methylpropanamide], a Diamide Diamine The protected diamide diamine (3200 gm, 5.95 mol), absolute ethanol (23 L), and hydrazine dihydrochloride (1376 gm. 13.1 mol) were charged to a flask. The slurry was warmed to 30° C. and then triethylamine (2633 gm, 26.0 mol) was added drop-wise over a 2 hr period. The reaction was heated during the triethylamine addition and a slight exotherm was observed. The solution slurry thinned as the $NEt_3$ was added. The final temperature at the end of the addition was 65° C. The reaction was heated to reflux (81° C.) for 28 hr. By-product precipitated from solution as the reaction progressed. The ethanol was removed under vacuum at 60° C. leaving a light brown/dark orange solid. The solid was dissolved in 17 L of deionized water. Sodium carbonate (2.54 kg) was added to the solution to bring the pH up to 11–12. The product was then extracted into methylene chloride (3×14.0 kg). The aqueous layer was discarded. The dichloromethane was removed under vacuum leaving a solid (1660 gm). The solid was slurried and stirred in acetone (1.83 kg) for 1 hr. The solid was recovered by filtration and then dried at 40° C. overnight. Yield: 973 gm (60%). $^1H$ NMR ($d_3$ $CD_3CN$) 7.59 (m, 2H), 6.99 (m, 2H), 2.57 (s (br), 4H), 1.28 (s, 12 H).

V. Synthesis of the Macrocyclic Tetraamido Compound ($H_4B^*$)*) 3,4,8,9-tetrahydro-3,3,6,6,9,-hexamethyl-1H-1,4,8,11-benzotetraazocyclotridecane-2,5,7,10 (6H, 11H) tetrone Dichloromethane (28 L) and dimethylmalonyl chloride (1815 gm, 10.72 mol) were charged to a 30 gallon glass lined reactor. The reactor was purged with nitrogen. The diamide diamine (2970 gm, 10.72 mol), triethylamine ($Et_3N$) (2385 gm, 23.58 mol), and dichloromethane (38 L) were charged to a 72 L flask. The solution was mixed until it became homogeneous. The 72 L flask was placed on a scale. The diamide diamine solution was pumped into the 30 gallon reactor containing the dichloromethane/dimethylmalonyl chloride solution using a FMI pump. The feed rate varied between 25–35 gm/min. The addition was complete in 36 hr. The reaction was allowed to mix for 2 hr after the addition was complete.

The solid in the 30 gallon reactor was allowed to settle. The dichloromethane was decanted from the solid. Methanol (55 L) was then charged to the reactor in order to dissolve the triethylammonium hydrochloride. The solution was mixed for 15 min and then the solid was allowed to settle. The methanol (64 L) was decanted from the solid. A second charge of methanol (63 L) was added to the solid, the suspension was mixed for 15 min. and then the solid allowed to settle. The second methanol wash was decanted from the solid. The remaining slurry was then filtered. The product particle size was very fine. After the vessel was empty and the filtration was complete the 30 gallon reactor was rinsed with 2 L of methanol. The wet-cake was dried in a vacuum oven at 40° C. and full vacuum for 48 hr. Yield: 2250 gm (55%). %). $^1$H NMR (d$_6$ DMSO) 8.41 (s, 2H), 7.70 (s, 2H), 7.48 (dd, 2H), 7.13 (dd, 2H), 1.47 (s, 12H), 1.44 (s, 6H).

Additional examples with different protected diamide diamines follow. Specific ones that have been used with at least one of the improved synthetic methods are 1,2-phenylenediamine, 4-nitro-1,2-phenylenediamine, and 3,4-diaminobenzoic acid methyl ester.

IV. Protected Ester Diamide Diamine

The protected esterdiamide diamine (8.5 g, 14 mmol) was placed in a round bottom flask fitted with a reflux condenser, and 100 mL of absolute ethanol was added. Hydrazine dihydrochloride (2.9 g, 30.8 mmol) was added and the solution was warmed a few minutes then triethylamine (7.7 mL, 61.6 mmol) was added. After refluxing for 15 minutes, the heterogeneous reaction mixture became almost homogeneous. After some time, a white precipitate began to form. The solution was refluxed overnight. The solution was cooled to room temperature and filtered. The solid was washed with ethanol then the ethanol removed on a rotary evaporator. The solid was taken up in water and the pH adjusted to 12. The solution turned yellow and it was then extracted with dichloromethane (4×150 mL). The dichloromethane was removed on a rotary evaporator, and the residual solid was washed with ether to obtain ester diamide diamine. Yield: 2.15 g, 45%. $^1$H NMR (d$_6$ DMSO) 9.62 (s, 1H), 9.41 (s,1H), 7.16 (m, 3H), 4.0 (s (br), 4H), 3.92 (s, 3H), 1.73 (d, 12H).

V. Synthesis of H$_4$EsterB*

The ester diamide diamine (400 mg, 1.2 mmol) was dissolved in about 15 mL CH$_2$Cl$_2$ (ACS grade) containing 0.41 mL (2.5 mmol) of dry NEt$_3$. The solution was taken up in a syringe. In a round bottom flask containing 15 mL CH$_2$Cl$_2$ was placed (0.21 mL, 1.5 mmol) dimethylmalonyl chloride. The ester diamide diamine mixture was added dropwise over about 6 h to the dimethylmalonyl chloride solution using a syringe pump. A white solid formed during the addition. After the addition complete, the reaction was stirred for 3 hours. The CH$_2$Cl$_2$ was then stripped off, the white solid was washed with water. The residual solid was washed with ether and dried at 60° C. for 4–6 h to obtain H$_4$EsterB*. Yield: 380 mg, 70%. Characterization: $^1$H NMR (d$_6$-DMSO, δ ppm): 8.5 (s, 1H, amide NH), 8.4 (s, 1H, amide NH), 7.95 (d, 1H, amide NH), 7.8 (d, 1H, amide NH), 7.7 (m, 3H, ArH), 3.8 (s, 3H, ester), 1.56 (s, 12H, R$_1$CH$_3$), 1.54 (s, 6H, R$_2$CH$_3$). IR (KBr Pellet) ν [cm$^{-1}$]: 3397 (s, m, amide NH), 3324 (s, str, amide NH), 1730 (s, str, ester), 1699 (s, str, amide CO), 1683 (s, str, amide NH), 1660 (s, str, amide CO), 1633 (s, str, amide CO), 1210 (s, str, ester), 1185 (s, str, ester). Anal. Calc'd. for C$_{21}$H$_{28}$N$_4$O$_6$: C 55.99, H 6.71, N 12.44. Found: C 56.08, H 6.53, N 12.58. MS (ESI) neg. ion mode m/z (relative intensity): 432 (M–H$^+$, 100)

Synthesis of H$_4$AcidB*

The H$_4$Ester B* (200 mg, 0.5 mmol) was placed in a round bottom flask fitted with a reflux condenser and 10 mL of 95% ethanol was added. Then, KOH (0.25 g, 5 mmol) was added and the reaction mixture was refluxed about 4 h. The solution was cooled to room temperature and the solvent was removed on the rotary evaporator. The solid was dissolved in water and the pH of the solution was adjusted to 2–3. The product precipitated from the solution. The flask with the solid was placed in a refrigerator for 1 h and then the solid was recovered by filtration. Yield: 0.16 g, 83%. Characterization: $^1$H NMR (d$_6$-DMSO, δ ppm): 8.5 (s, 1H, amide NH), 8.4 (s, 1H, amide NH), 7.95 (d, 1H, amide NH), 7.8 (d, 1H, amide NH), 7.7 (m, 3H, ArH), 1.56 (s, 12H, R$_1$CH$_3$), 1.54 (s, 6H, R$_2$CH$_3$). IR (KBr Pellet) ν [cm$^{-1}$]: 3394 (s, m, amide NH), 2985 (s, str, amide NH), 1691 (s, str, amide CO), 1683 (s, str, amide NH), 1660 (s, str, amide CO), 1633 (s, str, amide CO), 1419 (s, str, acid). Anal. Calc'd. for C$_{20}$H$_{22}$N$_4$O$_6$: C 56.41, H 6.26, N 12.69. Found: C 56.11, H 6.16, N 12.85. MS (ESI) neg. ion mode m/z (relative intensity): 418 (M–H$^+$, 100)

IV. Synthesis of Nitrodiamide Diamine

The protected nitrodiamide diamine (46 g, 85 mmol) was placed in a round bottom flask fitted with a reflux condenser, and 250 mL of absolute ethanol was added. Hydrazine dihydrochloride (18.2 g, 187 mmol) was added and the solution was warmed a few minutes then triethylamine (48 mL, 374 mmol) was added. After refluxing for 15 minutes, the heterogeneous reaction mixture became almost homogeneous. After some time, a white precipitate began to form. The solution was refluxed overnight. The solution was cooled to room temperature and filtered. The solid was washed with ethanol then the solid was taken up in water and the pH adjusted to 12. The solution turned yellow and it was then extracted with dichloromethane (4×150 mL). The dichloromethane was removed on a rotary evaporator, and the residual solid was washed with ether to obtain nitro diamide diamine. Yield: 10 g. 43%. $^1$H NMR (d$_6$ DMSO) 8.5 (d, 2H), 8.1 (s, 1H), 8.13 (s, 2H), 5.2 (s (br), 4H), 3.92 (s, 3H), 1.4 (d, 12 H).

V. Synthesis of NitroB*

The nitro diamide diamine (2.6 g, 8 mmol) was dissolved in about 40 mL CH$_2$Cl$_2$ (ACS grade) containing 2.25 mL (16 mmol) of dry NEt$_3$ and then taken up in a syringe. In a round bottom flask containing 20 mL CH$_2$Cl$_2$ was placed (1.18 mL, 8.8 mmol) dimethylmalonyl chloride. The nitro diamide diamine mixture was added dropwise over about 20 min. to the dimethylmalonyl chloride solution using a syringe pump. A white solid formed during the addition. After the addition complete, the reaction was stirred for 3 hours. The CH$_2$Cl$_2$ was then removed in vacuo and the white solid washed with water then diethyl ether and then dried at 60° C. for 4–6 h to obtain H$_4$NitroB*. Yield: 3.5 g, 100%. Characterization: $^1$H NMR (d$_6$-DMSO, δ ppm): 8.73 (s, 1H, amide NH), 8.58 (s, 1H, amide NH), 8.22 (d, 1H, amide NH), 8.08 (d, 1H, amide NH), 7.85 (s, 1H, ArH), 7.82 (s, 1H, ArH), 7.7 (d, 1H, ArH), 1.49 (s, 12H, R$_1$CH$_3$), 1.45 (s, 6H, R$_2$CH$_3$). IR (KBr Pellet) ν [cm$^{-1}$]: 3397 (s, m, amide NH), 3324 (s, str, amide NH), 1699 (s, str, amide CO), 1683 (s, str, amide NH), 1635 (s, str, amide CO), 1589 (s, str, amide CO), 1509 (s, nitro). Anal. Calc'd. for C$_{19}$H$_{21}$N$_5$O$_6$: C 52.17, H 6.22, N 16.01. Found: C 52.69, H 5.97, N 15.99. MS (ESI) neg. ion mode m/z (relative intensity): 418 (M–H$^+$, 100)

Synthesis of Metal Complexes

Formation of LiFeB*

The following reaction needs to be performed under anhydrous conditions because of the use of a pyrophoric, n-BuLi, and a water sensitive reagent $FeCl_3$.

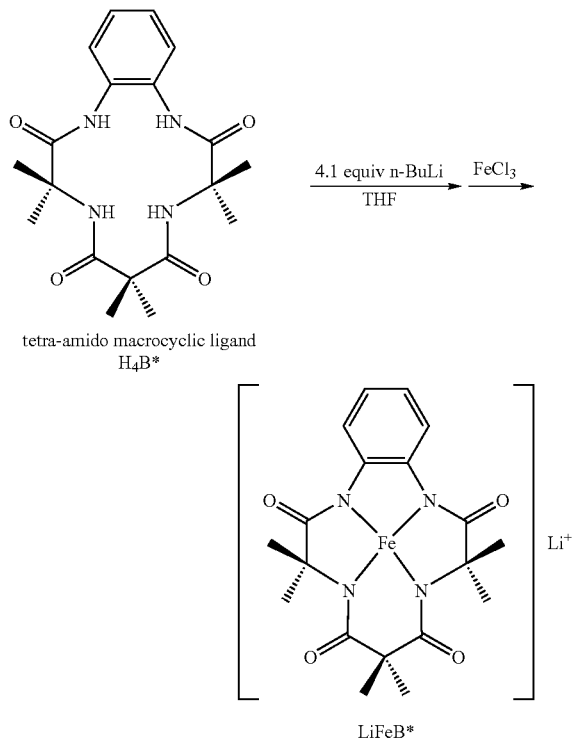

tetra-amido macrocyclic ligand
$H_4B^*$

LiFeB*

A 22.74 g (0.06 mol) quantity of the tetra-amido macrocyclic ligand, $H_4B^*$, was placed in a round bottom flask with a stir bar. A dry, inert atmosphere was established then 500 mL of anhydrous THF was added to the flask. The slurry was stirred and then n-BuLi 100 mL of 2.5 M in hexanes (0.25 mol) was added to the slurry. Gas evolution was very rapid and the reaction rapidly reached reflux temperature. It is likely that reflux is necessary for full deprotonation of the ligand and n-BuLi addition should be controlled to allow for reflux to occur. The reaction solution darkened during n-BuLi addition and when it was complete, a homogenous solution was present with no gas evolution. This solution was stirred for 10 min. and then solid $FeCl_3$, 10.8 g (0.067 mol) was added. Reaction is very rapid and an orange brown solid formed, LiFeB* is insoluble in THF. After addition was completed, the reaction was stirred and heated for approximately 4 hrs, cooled to room temperature, and then filtered. The filtrate was almost colorless. The solid was washed with THF and then $Et_2O$ to aid in drying. The solid was dissolved in 2-propanol (~1 L) giving a very dark orange brown solution. This solution was filtered through filter-aid and then the 2-propanol was removed in vacuo producing 30 g of solid.

Elemental analysis of this solid shows an almost pure product. The product is believed to be useable in this form. It may contain a small amount of LiCl above stoichiometric as well as solvent molecules, THF and 2-propanol. Further purification procedures are optional. Removal of LiCl can be achieved by re-suspension in THF, filtration, and drying of the solid. Analytically pure materials are obtained by dissolving the solid in water, filtering, adding iso-propanol, and removing all of the liquids in vacuo. The iso-propanol aids in removing the water without foaming. Calc'd (found) for LiFeB*.3/2LiCl.$6H_2O$.$2(C_3H_8O)$ MW=725.1, % C=41.41 (41.44), % H=6.95 (6.99), % N=7.73 (7.34), % Cl=7.33 (7.02)

$Li_2[Fe(H_2O)AcidB^*]$ $H_4AcidB^*$ (107 mg, 0.256 mmol) was placed in a round bottom flask and then an inert atmosphere was established using standard techniques. Dry THF (15 mL, dried over Na/benzophenone) was added and the mixture was stirred under $N_2$. $Li\{[(CH_3)_3Si]_2N\}$ under $N_2$ (1.4 mL, 1.4 mmol, 1 M in THF) was added to the $H_4AcidB^*$ suspension at 25° C. The resulting solution was stirred for 5 min, and then the $FeCl_2$ (48 mg, 0.38 mmol) was added. An orange precipitate formed almost immediately and the suspension was stirred overnight. Air was admitted though a drying tube for about 1 h, and the precipitate was collected and washed with $CH_2Cl_2$ (40 mL). The resulting product was purified by eluting though a C-18 silica gel column with 98% $H_2O$ and 2% $CH_3OH$. The $H_2O$ was removed under reduced pressure to yield a orange powder. Yield: 80 mg (66%). Characterization: IR (nujol/NaCl) $v[cm^{-1}]$: 1681, 1573, & 1456 (amide CO), 1384 (acid). Anal. Calc'd for $C_{20}H_{22}N_4O_6FeLi.(H_2O)_3$: C 45.22, H 5.31, N 10.55. Found: C 45.43, H 4.98, N 10.40. MS (ESI) neg. ion mode m/z (relative intensity): 470 (M–$H^+$, 100).

$Li[Fe(H_2O)EsterB^*]$

This complex was synthesized from $H_4EsterB^*$ (100 mg, 0.23 mmol), $FeCl_2$ (44 mg, 0.35 mmol), and $Li\{[(CH_3)_3Si]_2N\}$ (1 mL, 0.99 mmol, 1 M in THF) using the same procedure that is described above for $Li_2[Fe(H_2O)AcidB^*]$. Yield: 59 mg, 52%. Characterization: IR (nujol/NaCl) $v[cm^{-1}]$: 1695, 1614, & 1575 (amide CO), 1394, 1294 & 1261 (ester). Anal. Calc'd for $C_{21}H_{24}N_4O_6FeLi.(H_2O)_2(CH_3OH)$: C 47.25, H 5.77, N 10.02. Found: C, 47.05; H, 5.91; N, 10.21. MS (ESI) neg. ion mode m/z (relative intensity): 484 (M–$H^+$, 100).

$Li[Fe(H_2O)NO_2B^*]$

This complex was synthesized from $H_4NitroB^*$ (260 mg, 0.62 mmol), $FeCl_2$ (117 mg, 0.93 mmol), and $Li\{[(CH_3)_3Si]_2N\}$ (2.67 mL, 2.66 mmol, 1 M in THF) using the same procedure that is described above for $Li[Fe(H_2O)EsterB^*]$. Yield: 210 mg, 72%. Characterization: IR (nujol/NaCl) $v[cm^{-1}]$: 1623, 1565, & 1475 (amide CO), 1386 & 1321 (nitro). Anal. Calc'd for $C_{19}H_{21}N_5O_6FeLi.(H_2O)(CH_3OH)_3$: C 44.61, H 5.96, N 11.82. Found: C 44.66, H 5.79, N 11.45. MS (ESI) neg. ion mode m/z (relative intensity): 471 (M–$H^+$, 100).

$Li[Fe(H_2O)CH_3B^*]$

This complex was synthesized from $H_4MethylB^*$ (200 mg, 0.52 mmol), $FeCl_2$ (98 mg, 0.78 mmol), and $Li\{[(CH_3)_3Si]_2N\}$ (2.2 mL, 2.23 mmol, 1 M in THF) using the same procedure that is described above for $Li[Fe(H_2O)EsterB^*]$. Yield: 180 mg, 81%. Characterization: IR (nujol/NaCl) $v[cm^{-1}]$: 1579, 1567, & 1486 (amide CO), 1197 (methyl). Anal. Calc'd for $C_{20}H_{24}N_4O_4FeLi.(H_2O)_3$: C 43.26, H 5.49, N 9.89. Found: C 43.96, H 5.27, N 9.78. MS (ESI) neg. ion mode m/z (relative intensity): 440 (M–$H^+$, 100).

$Li[Fe(H_2O)(CH_3)_2B^*]$

This complex was synthesized from $H_4DimethylB^*$ (300 mg, 0.75 mmol), $FeCl_2$ (141 mg, 1.12 mmol), and $Li\{[(CH_3)_3Si]_2N\}$ (3.2 mL, 3.225 mmol, 1 M in THF) using the same procedure that is described above for $Li[Fe(H_2O)$ DimethylB*]. Yield: 175 mg, 78%. Characterization: IR (nujol/NaCl) v [cm$^{-1}$]: 1614, 1573, & 1524 (amide CO), 1484, 1454 & 1409 (methyls). Anal. Calc'd for $C_{21}H_{26}N_4O_4FeLi \cdot (H_2O)_4(CH_3OH)$: C 46.74, H 6.78, N 9.91. Found: C, 46.30; H, 6.41; N, 10.03. MS (ESI) neg. ion mode m/z (relative intensity): 454 (M–H$^+$, 100).

The invention claimed is:

1. A method for making a macrocyclic tetraamido compound comprising:
   protecting an amino portion of an amino carboxylic acid at a first temperature sufficient to form the protected amino carboxylic acid;
   without first isolating the protected amino carboxylic acid, mixing the protected amino carboxylic acid with a first solvent;
   without first isolating the protected amino carboxylic acid or the first solvent, converting the carboxylic acid portion of the protected amino carboxylic acid to an activated carboxylic acid to form a protected amino activated carboxylic acid derivative;
   without first isolating the protected amino activated carboxylic acid derivative, reacting the protected amino activated carboxylic acid derivative with a diamine in the presence of a second solvent and a base to form a protected diamide diamine intermediate;
   isolating the protected diamide diamine intermediate;
   deprotecting the diamide diamine intermediate; and,
   reacting the diamide diamine intermediate with an activated diacid to form the macrocyclic tetraamido compound having at least 11 atoms forming the macrocycle.

2. The method recited in claim 1 wherein protecting the amino portion of the amino carboxylic acid comprises reacting the amino carboxylic acid with an anhydride.

3. The method recited in claim 2 wherein the anhydride is selected from the group consisting of phthalic anhydride, substituted phthalic anhydride, and 2,3-diphenylmaleic anhydride.

4. The method recited in claim 1 wherein the first solvent is a hydrocarbon solvent that does not react with activating agents suitable for converting the protected amino carboxylic acid to the protected amino activated carboxylic acid derivative.

5. The method recited in claim 4 wherein the first solvent is toluene.

6. The method recited in claim 5 wherein the protected amino carboxylic acid is added to the toluene.

7. The method recited in claim 4 wherein the second solvent is THF in the presence of a base.

8. The method recited in claim 7 wherein the base is selected from the group consisting of triethylamine, tertiary amines and heterocyclic bases.

9. A method for making a macrocyclic tetraamido compound comprising:
   protecting an amino portion of an amino carboxylic acid at a first temperature sufficient to form the protected amino carboxylic acid;
   exposing the protected amino carboxylic acid to a first hydrocarbon solvent;
   converting the carboxylic acid portion of the protected amino carboxylic acid to an activated carboxylic acid to form a protected amino activated carboxylic acid derivative;
   reacting the protected amino activated carboxylic acid derivative with a diamine in the presence of a second dihaloalkane solvent and a base to form a protected diamide diamine intermediate; deprotecting the diamide diamine intermediate; and,
   reacting the diamide diamine intermediate with an activated diacid to form the macrocyclic tetraamido compound having at least 11 atoms forming the macrocycle.

10. The method recited in claim 9 wherein the dihaloalkane for the second solvent is selected from one of 1,2-dichloroethane, dichloromethane, dibromomethane and 1,2-dibromoethane.

11. The method recited in claim 1 wherein the first solvent is a dihaloalkane.

12. The method recited in claim 11 wherein the dihaloalkane for the first solvent is selected from one of 1,2-dichloroethane, dichloromethane, dibromomethane and 1,2-dibromoethane.

13. The method recited in claim 11 wherein the dihaloalkane is added to the protected amino carboxylic acid.

14. The method recited in claim 11 wherein the second solvent is selected from solvents that do not react with the protected amino activated carboxylic acid derivatives and do not cause the diamine to precipitate.

15. The method recited in claim 11 wherein the second solvent is a dihaloalkane.

16. The method recited in claim 15 wherein the dihaloalkane for the second solvent is selected from one of 1,2-dichloroethane, dichloromethane, dibromomethane and 1,2-dibromoethane.

17. The method recited in claim 1 wherein the first temperature is in the range of 150 to 200° C.

18. The method recited in claim 1 wherein the first temperature is in the range of 155–190° C.

19. The method recited in claim 1 wherein the first temperature is in the range of 175–190° C.

20. The method recited in claim 1 wherein converting the carboxylic acid portion of the protected amino carboxylic acid to an activated carboxylic acid derivative proceeds by acid halide formation.

21. The method recited in claim 20 wherein acid halide formation comprises reacting the protected amino carboxylic acid with one of an organic acid chloride or bromide, an inorganic acid chloride or bromide, or $H_2SiI_2$.

22. The method recited in claim 21 wherein the inorganic acid halide is thionyl chloride.

23. The method recited in claim 22 wherein the thionyl chloride is present in amounts ranging from about 0.9 to 1.5 molar equivalents based on the quantity of amino carboxylic acid.

24. The method recited in claim 22 wherein the thionyl chloride and the protected amino carboxylic acid are heated to reflux for a period of time ranging from about 1 to five hours.

25. The method recited in claim 1 wherein the carboxylic acid portion of the amino carboxylic acid is converted to an activated carboxylic acid derivative by esterification.

26. The method recited in claim 25 wherein esterification comprises reacting the protected amino carboxylic acid with $BF_3 \cdot Et_2O$.

27. The method recited in claim 1 wherein the diamine is a substituted phenylene selected from the group consisting of 1,2-amino-4,5-X phenylene, wherein X is one of H, amino, halo, nitro, alkyl, alkoxy and amido, and 1,2-amino-4-X phenylene, wherein X is one of H, halo, ester, nitro, amino, alkyl, alkoxy and amido.

28. The method recited in claim 1 wherein deprotecting the diamide diamine intermediate comprises:

forming a solution of the protected diamide diamine intermediate in an alcohol with a compound having a functional group selected from the group consisting of hydrazine, a hydrazine derivative, a salt of hydrazine and a hydrate of hydrazine;

optionally adding a base;

heating to reflux for a period of time sufficient to remove the protective group and form a solid;

removing the alcohol;

dissolving the solid in water;

adjusting the pH to 7 or greater; and, extracting the diamide diamine intermediate.

29. A method for making macrocyclic tetraamido compounds comprising:

protecting an amino portion of an amino carboxylic acid at a first temperature sufficient to form the protected amino carboxylic acid;

exposing the protected amino carboxylic acid to a first solvent;

converting the carboxylic acid portion of the protected amino carboxylic acid to an activated carboxylic acid to form a protected amino activated carboxylic acid derivative;

reacting the protected amino activated carboxylic acid derivative with a diamine in the presence of a second solvent and a base to form a protected diamide diamine intermediate;

forming a solution of the protected diamide diamine intermediate in an alcohol with a hydrazine hydrate, wherein no additional base is added;

heating to reflux for a period of time sufficient to remove the protective group and form a solid;

removing the alcohol;

dissolving the solid in water;

adjusting the pH to between 7 and 10;

extracting the diamide diamine intermediate.; and, reacting the diamide diamine intermediate with an activated diacid to form the macrocyclic tetraamido compound having at least 11 atoms forming the macrocycle.

30. A method for making macrocyclic tetraamido compounds comprising:

protecting an amino portion of an amino carboxylic acid at a first temperature sufficient to form the protected amino carboxylic acid;

exposing the protected amino carboxylic acid to a first solvent;

converting the carboxylic acid portion of the protected amino carboxylic acid to an activated carboxylic acid to form a protected amino activated carboxylic acid derivative;

reacting the protected amino activated carboxylic acid derivative with a diamine in the presence of a second solvent and a base to form a protected diamide diamine intermediate;

forming a solution of the protected diamide diamine intermediate in an alcohol with one of hydrazine dihydrochloride or hydrazine acetate;

adding a base;

heating to reflux for a period of time sufficient to remove the protective group and form a solid;

removing the alcohol;

dissolving the solid in water;

adjusting the pH to greater than or equal to 10;

extracting the diamide diamine intermediate; and, reacting the diamide diamine intermediate with an activated diacid to form the macrocyclic tetraamido compound having at least 11 atoms forming the macrocycle.

31. The method recited in claim 30 wherein the base is triethylamine.

32. The method recited in claim 1 wherein the activated diacid is selected from the group consisting of oxalate, malonate and succinate activated derivatives.

33. The method of claim 32 wherein the malonate activated derivative has the general structure

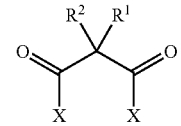

and the succinate activated derivative has the general structure

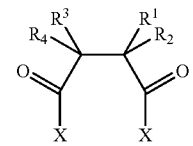

and the oxalate activated derivative has the general structure

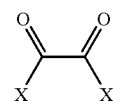

wherein X is halo or alkoxy and $R_1$, $R_2$, $R_3$ and $R_4$ are the same or different, and are selected from the group consisting of hydrogen, halo, aryl, amino, protected amino, nitro, sulphonyl, phosphoryl, silyl, carboxyl, siloxyl, sulfate, phosphate, ester, ether, imino, amido or alkyl, alkenyl or alkynyl, said alkyl, alkenyl, or alkynyl optionally substituted with carbonyl, and hidden amino selected from the group consisting of azide, azo, imido, isocyanate, isothiocyanate, nitrilium ions, nitro and phosphazo compounds.

34. The method recited in claim 32 wherein the malonate activated derivative is selected from the group consisting of disubstituted malonates, monosubstituted malonates and unsubstituted malonates.

35. The method of claim 1 wherein the diamine is selected from the group consisting of n,n+1 alkyl diamines, 1,2-aryl diamines, substituted n,n+2 alkyl diamines, substituted O-amino benzylamines and substituted 1,8-diamino napthalenes, wherein n is an integer greater than zero.

36. The method recited in claim 1 wherein the amino carboxylic acid is an α spiro-cyclohexyl-, spiro-cyclopentyl-, spiro-cyclobutyl-, or spiro-cycloproyl-amino carboxylic acid.

37. The method recited in claim 1 further comprising adding to the macrocyclic tetraamido compound under anhydrous conditions, a metal ion in the presence of a solvent and a base.

38. The method recited in claim 37 wherein the metal ion source is an Fe(III) compound.

39. The method recited in claim 38 wherein the metal ion is introduced as a metal halide, metal pseudohalide, or a metal ion with displaceable mono-, bi-, tri-, tetra-, penta-, or hexadentate ligands or combinations thereof sufficient to complete the coordination environment of the metal ion.

40. The method recited in claim 37 wherein the solvent is THF.

41. The method of claim 37 wherein the base is selected from the group consisting of lithium, sodium, or potassium bis-trimethylsilylamide, lithium, sodium or potassium di-isopropyl amide, t-butyl lithium, n-butyl lithium, phenyl lithium, and lithium or sodium dicyclohexylamide or an inorganic base such as lithium, sodium or potassium hydride.

42. The method recited in claim 1 further comprising complexing a transition metal to the macrocyclic tetraamido compound, said complexing comprising:
    suspending the macrocyclic tetraamido compound in a liquid;
    deprotonating the amides within the macrocycle of the macrocyclic tetraamido compound with a base; and,
    adding a metal ion.

43. The method recited in claim 42 further comprising adding an oxidizing agent.

44. The method recited in claim 43 wherein the added oxidizing agent is at least one of air, oxygen, chlorine, bromine or benzoyl peroxide.

45. The method of claim 42 wherein the base is selected from the group consisting of lithium, sodium, or potassium bis-trimethylsilylamide, lithium, sodium or potassium di-isopropyl amide, t-butyl lithium, n-butyl lithium, phenyl lithium, and lithium or sodium dicyclohexylamide or an inorganic base such as lithium, sodium or potassium hydride.

46. A method for making macrocyclic tetraamido compounds comprising:
    protecting an amino portion of an amino carboxylic acid at a first temperature sufficient to form the protected amino carboxylic acid;
    exposing the protected amino carboxylic acid to a dihaloalkane solvent;
    converting the carboxylic acid portion of the protected amino carboxylic acid to an activated carboxylic acid to form a protected amino activated carboxylic acid derivative;
    reacting the protected amino activated carboxylic acid derivative with a diamine in the presence of a second solvent and a base to form a protected diamide diamine intermediate;
    deprotecting the diamide diamine intermediate; and,
    reacting the diamide diamine intermediate with an activated diacid to form the macrocyclic tetraamido compound having at least 11 atoms forming the macrocycle.

* * * * *